US007841335B2

(12) United States Patent
Harrington et al.

(10) Patent No.: US 7,841,335 B2
(45) Date of Patent: Nov. 30, 2010

(54) NEBULIZER WITH FLOW-BASED FLUIDIC CONTROL AND RELATED METHODS

(75) Inventors: Steven M. Harrington, Cardiff by the Sea, CA (US); Douglas Gaylord, San Diego, CA (US); David A. Rivera, Yorba Linda, CA (US); Neil A. Korneff, Diamond Bar, CA (US); Rebecca A. Wilday, Riverside, CA (US); Chris Zollinger, Chino Hills, CA (US)

(73) Assignee: CareFusion 2200, Inc., San Diego, CA (US)

( * ) Notice: Subject to any disclaimer, the term of this patent is extended or adjusted under 35 U.S.C. 154(b) by 823 days.

(21) Appl. No.: 11/729,608

(22) Filed: Mar. 29, 2007

(65) Prior Publication Data

US 2007/0227535 A1 Oct. 4, 2007

Related U.S. Application Data

(60) Provisional application No. 60/787,195, filed on Mar. 30, 2006, provisional application No. 60/787,196, filed on Mar. 30, 2006.

(51) Int. Cl.
*A61M 11/00* (2006.01)

(52) U.S. Cl. ............................ 128/200.21; 128/200.18; 128/200.14

(58) Field of Classification Search ................................ 128/200.18–200.21, 202.28, 202.25, 203.11, 128/203.12, 203.15; 239/338
See application file for complete search history.

(56) References Cited

U.S. PATENT DOCUMENTS 4,116,387 A 9/1978 Kremer, Jr. et al.

(Continued)

FOREIGN PATENT DOCUMENTS

EP 0281650 A1 9/1988

(Continued)

OTHER PUBLICATIONS

PCT International Search Report mailed Oct. 2, 2007; 5 pages.

*Primary Examiner*—Steven O Douglas
(74) *Attorney, Agent, or Firm*—Dicke, Billig & Czaja, PLLC

(57) ABSTRACT

Various embodiments of a breath-activated nebulizer with flow-based fluidic control and related methods of using such a nebulizer are disclosed. The nebulizer may include a body comprising a reservoir for holding medication, a nozzle for emitting a jet of pressurized gas, and a fluid conduit in communication with the reservoir for delivery of the medication proximate the jet to produce an aerosol of medication. The nebulizer may also include a nebulizer outlet in communication with the body for delivery of the aerosol to a patient, an entrainment passage for providing entrainment flow from atmosphere during inhalation by the patient, and a control conduit in fluid communication with the fluid conduit for delivery of a control gas to the fluid conduit to prevent the delivery of the medication proximate the jet. In some exemplary embodiments, the control conduit may comprise a gas passage proximate the entrainment passage to allow the control gas to flow across the entrainment passage. During the inhalation by the patient, the entrainment flow through the entrainment passage may substantially prevent the control gas from flowing across the entrainment passage so as to interrupt the delivery of the control gas to the fluid conduit.

60 Claims, 19 Drawing Sheets

U.S. PATENT DOCUMENTS 4,560,519 A * 12/1985 Cerny ........................ 261/78.2
5,080,093 A * 1/1992 Raabe et al. ........... 128/203.12
6,595,203 B1 * 7/2003 Bird ...................... 128/200.21
6,644,304 B2 * 11/2003 Grychowski et al. ... 128/200.18
6,679,250 B2 * 1/2004 Walker et al. .......... 128/200.21

FOREIGN PATENT DOCUMENTS

EP 0855224 A2 7/1998
EP 0938906 A2 9/1999
FR 2751883 A1 2/1998
WO 03053500 A1 7/2003

* cited by examiner 1000
1140
1160
1190
1145
1180
92
98
1100

1140
1160
1190
92
1180
98

1100
1140
1148
1160
1145
1190

NEBULIZER WITH FLOW-BASED FLUIDIC CONTROL AND RELATED METHODS

This application claims the benefit of priority under 35 U.S.C. §119(e) of U.S. Provisional Application Nos. 60/787,195 and 60/787,196, both filed Mar. 30, 2006. This application also relates to commonly assigned U.S. application Ser. No. 11/729,720 of Steven M. Harrington et al., entitled "NEBULIZER WITH PRESSURE-BASED FLUIDIC CONTROL AND RELATED METHODS" and filed on the same date as the present application. The complete subject matter of each of the above-referenced applications is incorporated by reference herein.

FIELD OF THE INVENTION

Embodiments of the present invention relate generally to medical devices and related methods. More specifically, particular embodiments of the invention relate to a nebulizer system with flow-based fluidic control and related methods of using such a system.

DESCRIPTION OF RELATED ART

Nebulizers, also known as atomizers, are typically used to treat certain conditions or diseases that require medication to be delivered directly to the respiratory tract. To deliver medication to the respiratory tract, conventional nebulizers may use pressurized gas to nebulize liquid medication into aerosol that can be inhaled by a patient. In general, a reservoir containing the liquid medication or an orifice in communication with the reservoir is positioned adjacent an outlet of the pressurized gas, and when the pressurized gas passes over the reservoir or the orifice, a negative pressure is created in the vicinity of the outlet, causing the liquid medication to be drawn out of the reservoir and entrained into the stream of pressurized gas. The stream of pressurized gas with entrained liquid medication forms aerosol particles that are suspended within the nebulizer for inhalation by a patient.

In various conventional nebulizers, aerosol is continuously generated until the liquid medication in the reservoir is depleted. Such continuous nebulization causes a significant portion of the medication to be wasted into the environment when the patient is not inhaling. Also, it may be difficult to quantify the precise amount of aerosol that has been administered to the patient. To reduce such a waste, nebulizers with bag reservoir systems that collect generated aerosol between inhalations have been suggested. These systems, however, are bulky and difficult to set up. Moreover, studies have shown that a portion of the collected aerosol is deposited or condensed on the inner walls of the reservoir systems without ever being delivered to the patient.

Some nebulizers generate aerosol in a non-continuous manner, such as, for example, in response to a patient's breath. Such devices are more efficient than the above-mentioned, continuous nebulizers because the medication is not wasted when the patient is not inhaling. Certain nebulizers of this type utilize a movable diverter, positioned relative to the pressurized gas outlet or nozzle, to selectively nebulize the liquid medication. For example, the diverter may be movable between a non-nebulizing position and a nebulizing position in response to a patient's breath. When the patient is not inhaling, the diverter is in the non-nebulizing position (e.g., with a sufficient distance from the outlet of the pressurized gas) and no nebulization occurs in the nebulizer. Upon patient inhalation, a negative pressure is created inside the nebulizer, which causes the diverter to move to a nebulizing position (e.g., closer to the outlet of the pressurized gas) to divert the pressurized gas over the reservoir or the orifice of the reservoir. The high velocity air diverted over the reservoir or the orifice of the reservoir causes the liquid medication to be entrained and nebulized. At the end of the patient inhalation, the diverter is moved back to the non-nebulizing position by, for example, a spring, and the nebulization stops.

Nebulizers employing movable parts for actuation, however, have certain drawbacks. For example, while nebulizers are often intended for multiple uses, the aerosolized medication may dry out inside the nebulizer after use and may cause the movable parts to stick to non-moving parts, rendering the nebulizer inoperative for reuse. To eliminate the possibility of this sticking problem, the nebulizers may require thorough cleaning and/or disassembly of the nebulizer parts after each use. Moreover, the movable actuation system requires costly diaphragms and/or springs to actuate the movement of the moving parts. In addition, due to the relatively small tolerances required in such nebulizers (e.g., close control of the distance between the diverter and the gas outlet), design and manufacturing of movable actuation systems may pose difficulties.

Accordingly, there is a need for an improved nebulizer that may overcome one or more of the problems discussed above. In particular, there is a need for an improved actuation system with a minimum number of moving parts, while maintaining optimal performance.

SUMMARY OF THE INVENTION

Therefore, various exemplary embodiments of the invention may provide an improved nebulizer system with a stationary diverter and a flow-based fluidic control system to selectively actuate the nebulization process. There are several advantages of a nebulizer system with a fluidic control system. For example, in addition to its capabilities to overcome one or more problems discussed above, a fluidic control system, being extremely sensitive to pressure changes, may provide the potential of enabling control of the nebulization process at lower inspiratory flows than the conventional technology. This may result in faster and/or more consistent delivery of medication to the patient. Moreover, such fluidic control systems may allow a nebulizer system to be used on patients that may have the ability to produce only lower inspiratory flows, such as children or the elderly.

In addition, the flow-based control mechanism of the present invention may not require a significant level of negative pressure to initiate nebulization. Thus, a substantially less vacuum is needed to initiate nebulization, and a patient may experience less resistance during inhalation. Moreover, a lower threshold level of negative pressure may reduce the need to create a tighter seal at the patient interface (e.g., mouthpiece or face masks), thereby improving patient comfort.

While the present invention will be described in connection with a nebulizer system for nebulizing medication, embodiments of the invention may be used in other suitable medical and non-medical applications, such as, for example, veterinarian applications and on-demand humidification systems. Also, while the present invention will be described in connection with a breath-actuated nebulizer system, certain embodiments of the invention may include an interface device, such as a mechanical ventilator, for patients that are unable to breath enough on their own to trigger nebulization. In such cases, the interface device may be used to trigger the nebulizer system to nebulize liquid medication for delivery to the patient.

To attain the advantages and in accordance with the purpose of the invention, as embodied and broadly described herein, one exemplary aspect of the invention may provide a nebulizer comprising a body comprising a reservoir for holding medication, a nozzle for emitting a jet of pressurized gas, and a fluid conduit in communication with the reservoir for delivery of the medication proximate the jet to produce an aerosol of medication. The nebulizer may also comprise a nebulizer outlet in communication with the body for delivery of the aerosol to a patient, an entrainment passage for providing entrainment flow from atmosphere during inhalation by the patient, and a control conduit in fluid communication with the fluid conduit for delivery of a control gas to the fluid conduit to prevent the delivery of the medication proximate the jet. In some exemplary embodiments, the control conduit may comprise a gas passage proximate the entrainment passage to allow the control gas to flow across the entrainment passage. During the inhalation by the patient, the entrainment flow through the entrainment passage may substantially prevent the control gas from flowing across the entrainment passage so as to interrupt the delivery of the control gas to the fluid conduit.

In another exemplary aspect, the entrainment passage may comprise a venturi. The venturi may comprise an inlet in fluid communication with atmosphere and an outlet in fluid communication with an interior of the body. In another exemplary aspect, the gas passage may be disposed proximate a throat of the venturi. In still another exemplary aspect, the venturi may comprise a recessed portion adjacent the throat to facilitate the interruption of the control gas across the entrainment passage. In yet still another exemplary aspect, the venturi may be disposed inside the body.

In another aspect, the nebulizer may further comprise a flow guide positioned adjacent the gas passage. The flow guide may be configured to prevent the control gas from flowing across the entrainment passage during the inhalation by the patient.

According to one exemplary aspect, the gas passage may comprise an inlet port in fluid communication with the entrainment passage and an outlet port in fluid communication with the entrainment passage. The gas passage may be configured to transport the control gas from the inlet port to the outlet port across the entrainment passage. In some exemplary embodiments, the inlet port and the outlet port may be aligned in a direction substantially perpendicular to a longitudinal axis of the entrainment passage.

According to another exemplary aspect, the pressurized gas and the control gas may be delivered from a same source of gas. For example, the control gas may be drawn from a main gas line that supplies the pressurized gas to the nozzle. In some exemplary aspects, the nebulizer may further comprise a control flow manifold configured to direct the control gas drawn from the main gas line to the control conduit. The control flow manifold may comprise an opening in the main gas line.

In one exemplary aspect, the nebulizer may comprise a flow regulator for controlling a flow of the control gas. The flow regulator may comprise a through-hole in a sleeve that at least partially defines the fluid conduit. Alternatively or additionally, the flow regulator may comprise a valve disposed over an orifice in fluid communication with the control conduit, and the valve may be configured to open the orifice to vent excess control flow when the control gas flowing through the control conduit exceeds a threshold value.

According to another exemplary aspect, the gas passage may comprise an inlet port, and an outlet port facing the inlet port. The gas passage may be configured to transport the control gas from the inlet port to the outlet port across the entrainment passage, where the nebulizer may comprise a flow stopper movable between a first position, in which the stopper permits the flow of the control gas between the inlet and outlet ports, and a second position, in which the stopper substantially prevents the flow of the control gas across the entrainment passage. In various exemplary embodiments, the inhalation by the patient may cause the stopper to move from the first position to the second position.

In still another exemplary aspect, the movement of the flow stopper may be controlled by a valve (e.g., flapper valve or variable orifice valve) that moves in response to a patient's breath.

According to various exemplary aspects, the nebulizer may comprise a stationary diverter to which the jet of pressurized gas may be directed.

According to another exemplary aspect, the nebulizer may comprise an override mechanism configured to override breath actuation of the nebulizer. In some exemplary embodiments, the nebulizer may be configured to continuously generate the aerosol when the override mechanism may be actuated.

In still another exemplary aspect, the override mechanism may comprise a bypass conduit connecting between the control conduit and atmosphere and a valve disposed in the bypass conduit to open and close the bypass conduit. Upon actuation of the override mechanism, the valve may open the bypass conduit to vent the control gas from the control conduit to atmosphere, so as to prevent the delivery of the control gas to the fluid conduit.

According to some exemplary aspects, a nebulizer may comprise a body comprising a reservoir for holding medication, a nozzle for emitting a jet of pressurized gas, and a fluid conduit in communication with the reservoir for delivery of the medication proximate the jet to produce an aerosol of medication. The nebulizer may also comprise a nebulizer outlet in communication with the body for delivery of the aerosol to a patient, a control conduit in fluid communication with the fluid conduit for delivery of a control gas to the fluid conduit to prevent the delivery of the medication proximate the jet, a portion of the control conduit permitting a flow of the control gas across a gap, and a flow stopper movable between a first position, in which the stopper may be disposed out of the gap to permit the flow of the control gas across the gap, and a second position, in which the stopper may be disposed in the gap to substantially prevent the flow of the control gas across the gap. In various exemplary embodiments, the inhalation by the patient may cause the stopper to move from the first position to the second position.

In another exemplary aspect, the movement of the flow stopper may be controlled by a variable area orifice valve that actuates in response to the patient's inhalation. In still another exemplary aspect, the flow stopper may comprise a plate member movably disposed in and out of the gap. In yet still another exemplary aspect, the portion of the control conduit may be disposed in an entrainment passage that provides entrainment flow from atmosphere during the inhalation by the patient.

According to one exemplary aspect, the portion of the control conduit may comprise an inlet port and an outlet port facing the inlet port, so as to transport the control gas from the inlet port to the outlet port. A space between the inlet and outlet ports may define the gap.

In another exemplary aspect, the pressurized gas and the control gas may be delivered from a same source of gas. For example, the control gas may be drawn from a main gas line that supplies the pressurized gas to the nozzle. In some exemplary embodiments, the nebulizer may comprise a control flow manifold configured to direct the control gas drawn from the main gas line to the control conduit.

In still another exemplary aspect, the nebulizer may comprise a flow regulator for controlling a flow of the control gas. The flow regulator may comprise a through-hole in a sleeve that at least partially defines the fluid conduit.

According to still another exemplary aspect, the nebulizer may comprise a stationary diverter to which the jet of pressurized gas may be directed.

According to yet still another exemplary aspect, the nebulizer may comprise an override mechanism configured to override breath actuation of the nebulizer. The override mechanism may comprise a bypass conduit connecting between the control conduit and atmosphere and a valve disposed in the bypass conduit to open and close the bypass conduit. Upon actuation of the override mechanism, the valve may open the bypass conduit to vent the control gas from the control conduit to atmosphere, so as to prevent the delivery of the control gas to the fluid conduit.

Some exemplary aspects may provide a method of controlling a nebulization process. The method may comprise providing medication in a reservoir within a body, where the body comprises an outlet for delivery of medication to a patient and an entrainment passage for providing entrainment flow from atmosphere during inhalation by the patient, emitting a jet of pressurized gas into the body, and providing a fluid conduit in communication with the reservoir for delivery of the medication proximate the jet. The method may also comprise preventing delivery of the medication proximate the jet by delivering a control gas to the fluid conduit via a control conduit, where the control conduit comprises a gas passage proximate the entrainment passage to allow the control gas to flow across the entrainment passage, and interrupting the flow of the control gas across the entrainment passage to prevent the delivery of the control gas to the control conduit, where the interruption may permit delivery of the medication proximate the jet to produce an aerosol of medication.

In another exemplary aspect, during the inhalation by the patient, the entrainment flow through the entrainment passage may substantially interrupt the flow of the control gas across the entrainment passage.

According to one exemplary aspect, the entrainment passage may comprise a venturi. In another exemplary aspect, the gas passage may be disposed proximate a throat of the venturi.

In another exemplary aspect, the method may further comprise providing a flow guide adjacent the gas passage proximate the entrainment passage to prevent the control gas from flowing across the entrainment passage during the inhalation by the patient.

In some exemplary aspects, the gas passage may comprise an inlet port in fluid communication with the entrainment passage and an outlet port in fluid communication with the entrainment passage. The gas passage may be configured to transport the control gas from the inlet port to the outlet port across the entrainment passage.

In another exemplary aspect, the method may comprise providing a flow stopper movable between a first position, in which the stopper may permit the flow of the control gas between the inlet and outlet ports, and a second position, in which the stopper may substantially prevent the flow of the control gas across the entrainment passage, where the inhalation by the patient may cause the stopper to move from the first position to the second position.

According to still another exemplary aspect, the pressurized gas and the control gas may be delivered from a same source of gas. For example, the control gas may be drawn from a main gas line that supplies the pressurized gas.

In yet still another exemplary aspect, the method may comprise regulating a flow of the control gas to the control conduit via a flow regulator. In some exemplary embodiments, the flow regulator may comprise a valve disposed over an orifice in fluid communication with the control conduit, and the valve may be configured to open the orifice to vent excess control flow when the control gas flowing through the control conduit exceeds a threshold value. Alternatively or additionally, the method may comprise regulating a flow of the control gas via a through-hole in a sleeve that at least partially defines the fluid conduit.

In one exemplary aspect, the method may comprise directing the jet of pressurized gas towards a stationary diverter.

In another exemplary aspect, the method may comprise overriding the control of the nebulization process to continuously generate the aerosol of medication. The overriding may comprise providing a bypass conduit connecting between the control conduit and atmosphere, disposing a valve in the bypass conduit, and opening the valve to open the bypass conduit so as to vent the control gas from the control conduit to atmosphere.

According to one exemplary aspect of the invention, a method of controlling a nebulization process may comprise providing medication in a reservoir within a body, where the body comprises an outlet for delivering medication to a patient, emitting a jet of pressurized gas into the body, providing a fluid conduit in communication with the reservoir for delivery of the medication proximate the jet, and preventing delivery of the medication proximate the jet by delivering a control gas to the fluid conduit via a control conduit, where a portion of the control conduit permits a flow of the control gas across a gap. The method may also comprise providing a flow stopper movable between a first position, in which the stopper may be disposed out of the gap to permit the flow of the control gas across the gap, and a second position, in which the stopper may be disposed in the gap to substantially prevent the flow of the control gas across the gap. In various exemplary embodiments. The method may also comprise interrupting the flow of the control gas across the gap by the flow stopper to prevent the delivery of the control gas to the control conduit, where the interruption may permit delivery of the medication proximate the jet to produce an aerosol of medication.

In another exemplary aspect, the flow stopper may be movable from the first position to the second position in response to the inhalation by the patient.

In some exemplary aspects, the movement of the flow stopper may be controlled by a valve that actuates in response to the patient's inhalation.

According to one exemplary aspect, the portion of the control conduit may be disposed in an entrainment passage that provides entrainment flow from atmosphere during the inhalation by the patient.

In another exemplary aspect, the flow stopper may comprise a plate member movably disposed in and out of the gap.

According to another exemplary aspect, the portion of the control conduit may comprise an inlet port and an outlet port facing the inlet port, so as to transport the control gas from the inlet port to the outlet port. A space between the inlet and outlet ports may define the gap.

In some exemplary aspects, the pressurized gas and the control gas may be delivered from a same source of gas. In an exemplary embodiment, the control gas may be drawn from a main gas line that supplies the pressurized gas.

According to one exemplary aspect, the method may comprise regulating a flow of the control gas to the control conduit via a flow regulator. The flow regulator may comprise a valve disposed over an orifice in fluid communication with the control conduit, where the valve may be configured to open the orifice to vent excess control flow when the control gas flowing through the control conduit exceeds a threshold value. Alternatively or additionally, the method may comprise regulating a flow of the control gas via a through-hole in a sleeve that at least partially defines the fluid conduit.

In another exemplary aspect, the method may comprise directing the jet of pressurized gas towards a stationary diverter.

In still another exemplary aspect, the method may comprise overriding the control of the nebulization process to continuously generate the aerosol of medication. In some exemplary embodiments, the overriding may comprise providing a bypass conduit connecting between the control conduit and atmosphere, disposing a valve in the bypass conduit, and opening the valve to open the bypass conduit so as to vent the control gas from the control conduit to atmosphere.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

DESCRIPTION OF THE EMBODIMENTS

Reference will now be made in detail to exemplary embodiments consistent with the present invention, examples of which are illustrated in the accompanying drawings. Wherever possible, the same reference numbers will be used throughout the drawings to refer to the same or like parts.

Figure 1:
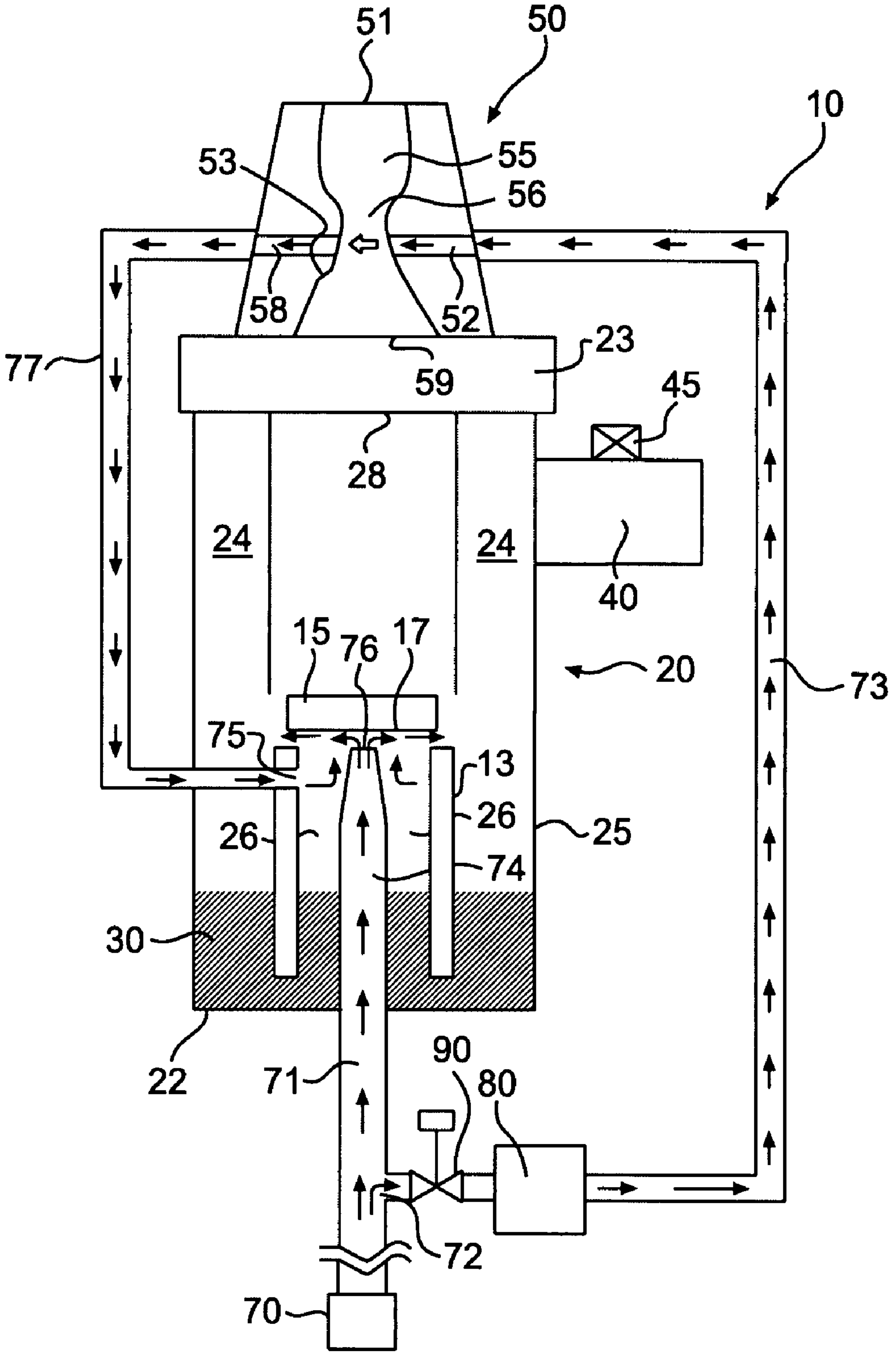
FIG. 1 is a schematic view of a nebulizer, according to an exemplary embodiment of the invention, illustrating a non-nebulizing mode.
Figure 2:
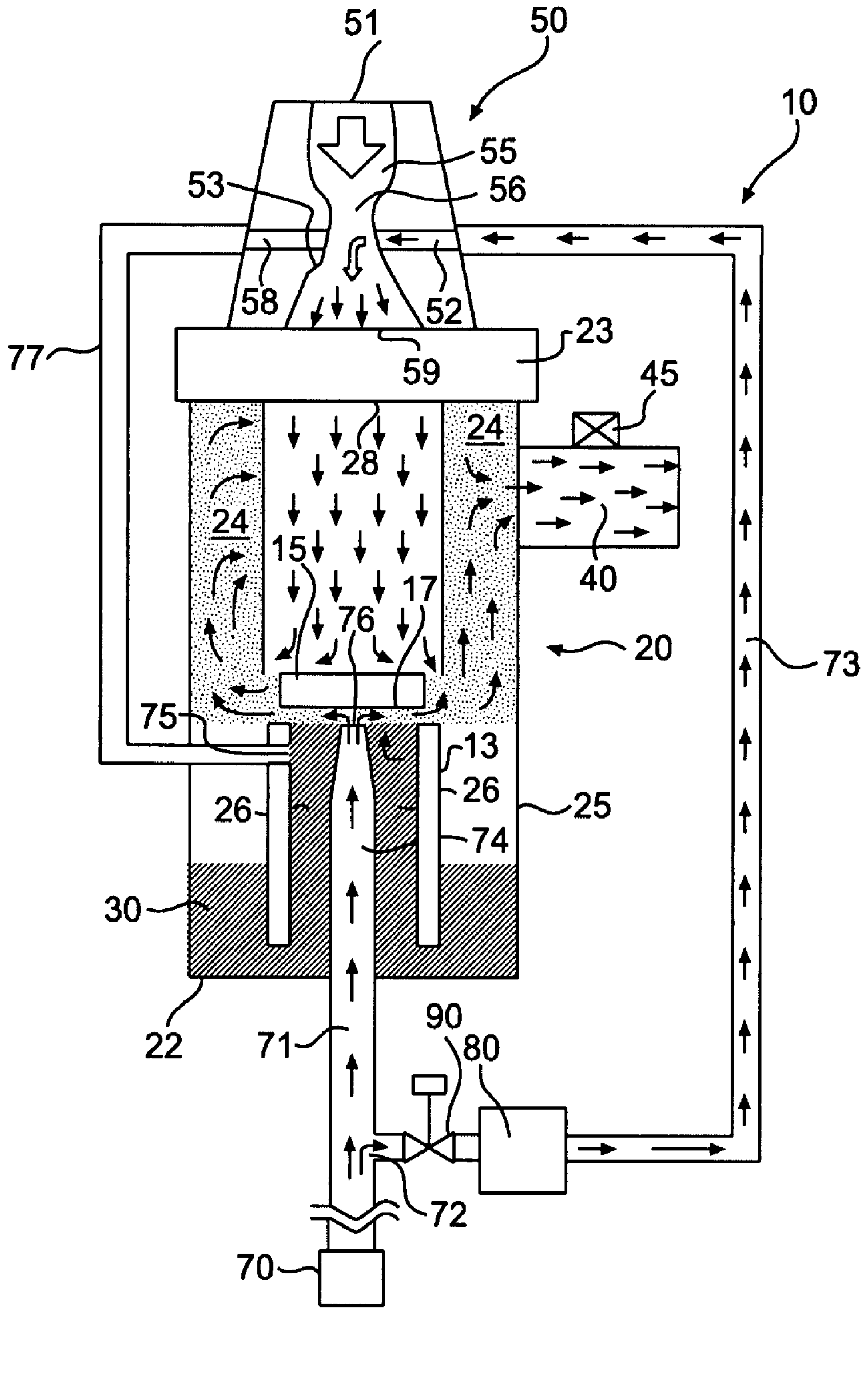
FIG. 2 is a schematic view of the nebulizer of FIG. 1, illustrating a nebulizing mode.

FIGS. 1 and 2 show a breath-actuated nebulizer 10 with a flow-based fluidic control mechanism, according to an exemplary embodiment of the invention. The nebulizer 10 may comprise a nebulizer body 20 defining an interior space 24 and an aerosol outlet port 40 in fluid communication with the interior space 24 for delivery of nebulized medication to a patient. The nebulizer 10 may also comprise a pressurized gas source 70 (e.g., at approximately 50 psi) for use in generating an aerosol jet during nebulization. As will be explained in more detail below, the fluidic control mechanism may selectively actuate a nebulization process within the nebulizer 10 in response to patient's breath (e.g., patient's inhalation through aerosol outlet port 40).

The nebulizer body 20 may comprise a generally cylindrical body 25 defining the interior space 24 and a fluid reservoir 22 for containing medication 30 intended for nebulization. The medication 30 may be in the form of liquid. The fluid reservoir 22 may have a variety of different shapes and sizes. For example, in some exemplary embodiments, the reservoir 22 may have a substantially conical or frusto-conical shape with its vertex portion pointing downward. The outlet port 40 (e.g., a mouthpiece) may extend from the body 25 and communicate with the interior 24 for delivery of nebulized medication to a patient. In some exemplary embodiments, the outlet port 40 may include a relief valve 45 (e.g., a one-way check valve) configured to direct flow from the patient during exhalation to atmosphere.

An air entrainment port 28 may be positioned at an upper portion of the nebulizer body 20 and may be in fluid communication with atmosphere via a fluidic control switch 50 (e.g., a jet disruption venturi). As will be described further herein, the fluidic control switch 50 may be configured to selectively switch the operational condition of the nebulizer 10 between a non-nebulizing mode and a nebulizing mode in response to patient inhalation.

Although not necessary, in some exemplary embodiments, a pressure regulator 23 may be disposed in the entrainment port 28 to control air entrainment flow into the interior space 24 during the patient inhalation. A certain threshold level of vacuum inside the interior space 24 may aid the actuation of the fluidic control switch 50, and the pressure regulator 23 at the air entrainment port 28 may be used to maintain the interior space 24 at an optimal vacuum level during the patient inhalation. For example, when the patient inhales, a vacuum is created in the interior space 24. After a predetermined threshold vacuum is reached, the normally-closed pressure regulator 23 may open to allow outside air to entrain into the interior space 24. Opening the pressure regulator 23 may eliminate any excessive resistance to the patient inhalation caused by excessive vacuum in the interior space 24, while maintaining the vacuum above the threshold level. In one exemplary embodiment, the pressure regulator 23 may include one or more openings, the size of which may vary depending upon the flow rate of the entrained air. In another exemplary embodiment, the pressure regulator 23 may include a spring-loaded member, or other biased member such as a flexible valve or diaphragm, and may automatically fully close at the end of the patient inhalation. Of course, in some exemplary embodiments, the nebulizer 10 may not include any pressure regulator.

As shown in FIGS. 1 and 2, pressurized gas (e.g., air) from the pressurized gas source 70 may be directed towards a diverter 15 (e.g., a baffle) to cause nebulization of the medication 30. The diverter 15 is preferably stationary. In various exemplary embodiments, the pressurized gas may be accelerated through a nozzle 74 to an outlet 76 to create an aerosol jet impinging upon the diverter 15. The nozzle 74 may extend from the bottom of the nebulizer body 20 in a direction substantially parallel to a longitudinal axis of the nebulizer body 20. The outlet 76 of the nozzle 74 may face the diverter 15 in a direction substantially perpendicular to an impingement surface 17 of the diverter 15. Adjacent the diverter 15 and around the nozzle 74, a fluid sleeve 13 (e.g., annular sleeve) defining a conduit 26 (e.g., annular conduit) may be provided for transporting the medication 30 from the fluid reservoir 22 to the aerosol jet during nebulization. The distance between the outlet 76 of the nozzle 74 and the impingement surface 17 of the diverter 15 may be sufficiently close, such that, during nebulization, the pressurized gas diverted by the diverter 15 may create a sufficient negative pressure in the conduit 26 to cause the medication 30 to be transported up the conduit 26 and entrained into the aerosol jet for nebulization.

As mentioned above, the fluidic control mechanism of the present disclosure may selectively actuate the nebulization process in the nebulizer 10 in response to patient inhalation. For example, the fluidic control mechanism may utilize a flow of control gas ("control flow" hereinafter) to selectively interrupt the uptake of the medication 30 into the conduit 26, so as to prevent nebulization of the medication 30. The control flow may be supplied from the same pressurized gas source 70, as shown in FIGS. 1 and 2. To direct the control flow from the pressurized gas source 70, a control flow manifold 72 (e.g., a T-junction) may be positioned in the main pressurized gas line 71 to create a pressure drop therein and thereby create a low-flow (e.g., approximately 1-5 lpm), low-pressure (e.g., approximately 50-140 cm water) flow from the main pressurized gas line 71. The manifold 72 may use an orifice and/or varied geometries of its flow path to achieve the desired pressure drop. In an alternative embodiment, the control flow may be supplied from a separate gas source.

The nebulizer 10 may also include a control flow regulator 80 located, for example, between the control flow manifold 72 and the fluidic control switch 50. In some exemplary embodiments, the flow regulator 80 may be placed at any location along the nebulizer flow path 77 between the fluidic control switch 50 and the fluid conduit 26. The regulator 80 may be configured to maintain the control flow to the conduit 26 within a certain flow rate range. For example, when the flow rate of the control flow exceeds a specified threshold value, the control flow regulator 80 may vent excess flow out to atmosphere to maintain the control flow within a desired range. In an exemplary embodiment, such as the embodiment shown in FIG. 10, the control flow regulator 80 may include a weighted or spring-loaded float disposed over a fixed orifice, and when the control flow rate exceeds a specified threshold valve, the weighted float may be lifted to release the excess pressure to atmosphere. In some embodiments, the float may be held in place with a spring to lift the float. Any other suitable flow regulation techniques known in the art may also be used alternatively or additionally.

Maintaining the flow rate of the control flow within a certain range may be important for various reasons. For example, if the flow rate is too high, a greater entrainment flow (e.g., created by patient inhalation) may be required to actuate the fluidic control switch 50 to switch from the non-nebulizing mode to the nebulizing mode. In addition, the high flow rate may cause the control flow to flow down into the fluid reservoir 22, thereby causing undesirable bubbling in the reservoir 22. Moreover, it may be desirable to regulate gas entering the fluidic control switch 50 to account for various pressurizing gas systems with varying source pressures.

Figure 3:
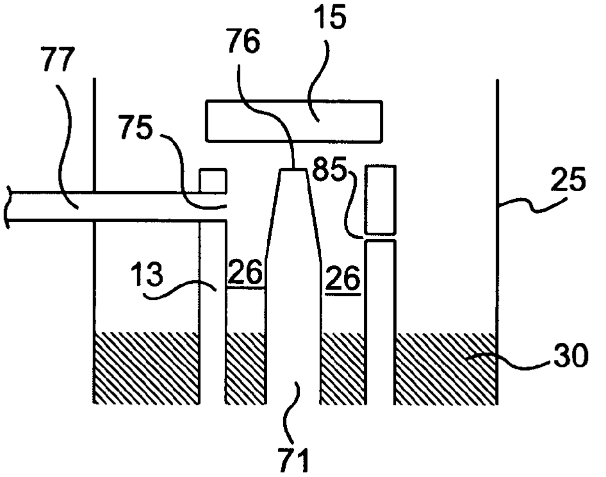
FIG. 3 is a partial schematic view of a nebulizer system, according to still another exemplary embodiment of the invention, illustrating an alternative or additional control flow regulator.

In some exemplary embodiments, the system 10 may regulate the control flow after it reached the fluid conduit 26. For example, in place of, or in addition to, the flow regulator 80 discussed above, the system 10 may include a through-hole 85 in the fluid sleeve 13, as shown in FIG. 3. The through-hole 85 may provide a flow passage for excessive control flow to vent out of the fluid conduit 26, thereby preventing the excessive control flow from reaching down the reservoir 22 and causing undesirable bubbling. The through-hole 85 may be positioned below the exit portion 75 of the nebulizer flow path 77 and at substantially opposite side facing the exit portion 75. The opening area of the through-hole 85 may be smaller than the opening area of the exit portion 75. By way of examples only, the through-hole 85 may have an opening area that is 0.4-0.6 times the opening area of the exit portion 75. The through-hole 85 may be sufficiently small such that, during nebulization, the liquid medication 30 may effectively seal or block the through-hole 85, preventing air from entering into the conduit 26 through the through-hole 85.

In various exemplary embodiments, the nebulizer 10 may include a suitable override mechanism configured to override breath actuation function of the nebulizer 10 to continuously generate aerosol. The override mechanism may be controlled manually or automatically. In various exemplary embodiments, the override mechanism may include a valve 90 configured to selectively open and close the control flow passage from the control flow manifold 72 to the conduit 26. Thus, the valve 90 may be disposed at any location between the control flow manifold 72 and the conduit 26. In one exemplary embodiment, as shown in FIGS. 1 and 2, the valve 90 may be placed near the control flow manifold 72 before the flow regulator 80. When the valve 90 is actuated, the valve 90 closes the control flow path to prevent the control flow from reaching the conduit 26, regardless of whether the patient is inhaling or not. Thus, the breath actuation function of the nebulizer system 10 may be disabled, and the nebulized medication may be continuously generated. When the valve 90 is not actuated, the valve 90 may be biased in an open position to enable the breath actuation function of the nebulizer 10.

As shown in FIGS. 1 and 2, the fluidic control switch 50 may comprise a venturi 55 associated with the nebulizer body 20. In various embodiments, the venturi 55 may be positioned above the nebulizer body 20, as shown in FIGS. 1 and 2, or inside the nebulizer body 20. In an alternative embodiment, the venturi 55 may be positioned at or near the outlet port 40. The venturi 55 may include an inlet 51 in fluid communication with atmosphere and an outlet 59 in fluid communication with the air entrainment port 28 of the nebulizer body 20. In the vicinity of a throat 56 of the venturi 55, the fluidic control switch 50 may include a jet inlet port 52 and a jet receiving port 58 substantially opposite the jet inlet port 52. The jet inlet port 52 and the jet receiving port 58 may be aligned in a direction substantially perpendicular to a longitudinal axis of the venturi 55. In some exemplary embodiments, the opening area of the jet receiving port 58 may be greater than the opening area of the jet inlet port 52 to facilitate receiving of the control flow jet from the jet inlet port 52. The jet inlet port 52 may be in fluid communication with an inlet flow path 73 to receive the control flow from the pressurized gas source 70, and the jet outlet port 58 may be in fluid communication with a nebulizer flow path 77 for directing the control flow to an upper portion of the conduit 26 defined by the fluid sleeve 13. The fluid sleeve 13 may define an opening through which an exit port 75 of the nebulizer flow path 77 may pass to communicate with the conduit 26.

When the control flow is permitted to enter the conduit 26 of the fluid sleeve 13, the control flow may function as a substitute fluid, in place of the medication 30 in the reservoir 22, to compensate for the negative pressure created by the aerosol jet in the vicinity of the diverter 15. Thus, the control flow entering the conduit 26 may disrupt or prevent the medication 30 from being transported up the conduit 26 for nebulization, thereby disrupting or preventing nebulization in the nebulizer 10. Conversely, interrupting the control flow to the conduit 26 may allow the medication 30 to be entrained into the conduit 26 and the aerosol jet, thereby initiating the nebulization in the nebulizer 10.

As an example, FIGS. 1 and 2 illustrate the direction of the control flow during a non-nebulizing mode and a nebulizing mode, respectively. Referring to FIG. 1, when the patient is not inhaling, the control flow entering the jet inlet port 52 may pass across the throat 56 of the venturi 55 in the direction perpendicular to the longitudinal axis of the venturi 55 and enter the jet receiving port 58 positioned opposite the jet inlet port 52. In this non-nebulizing mode, the control flow exiting the fluidic control switch 50 may then travel through the nebulizer flow path 77 and enter into the conduit 26 inside the fluid sleeve 13 to disrupt the uptake of the medication 30 into the conduit 26 and the aerosol jet.

Upon patient inhalation through the outlet port 40, as shown in FIG. 2, a negative pressure created at the outlet port 40, functioning as a triggering signal to disrupt the control flow to the conduit 26, may cause the entrainment port 28 to open (e.g., by opening the pressure regulator 23) and induce an entrainment flow of gas from atmosphere into the venturi 55. The entrainment flow may enter the venturi 55 via the inlet 51, pass through the throat 56, and exit the venturi 55 via the outlet 59. The entrainment flow through the venturi 55 may disrupt the stream of the control flow across the venturi 55 by pulling the control flow away from the jet receiving port 58 towards the outlet 59 of the venturi 55. As a result, the control flow may no longer reach the jet receiving port 58 and the conduit 26 of the fluid sleeve 13. The entrainment flow through the venturi 55, a velocity of which increases near the throat 56, may also contribute to the disruption of the control flow. For example, the high velocity entrainment flow through the venturi 55 may create a negative pressure at the jet receiving port 58, which may prevent the gas in the venturi 55 from entering the jet receiving port 58.

In various exemplary embodiments, to facilitate the disruption of the control flow, the venturi 55 may include a recessed portion 53 positioned below the jet receiving port 58. During the patient inhalation, the entrainment flow through the venturi 55 may create a low-pressure pocket in or near the recessed portion 53, which may help to pull the control flow away from the jet receiving port 58.

Figure 2A:
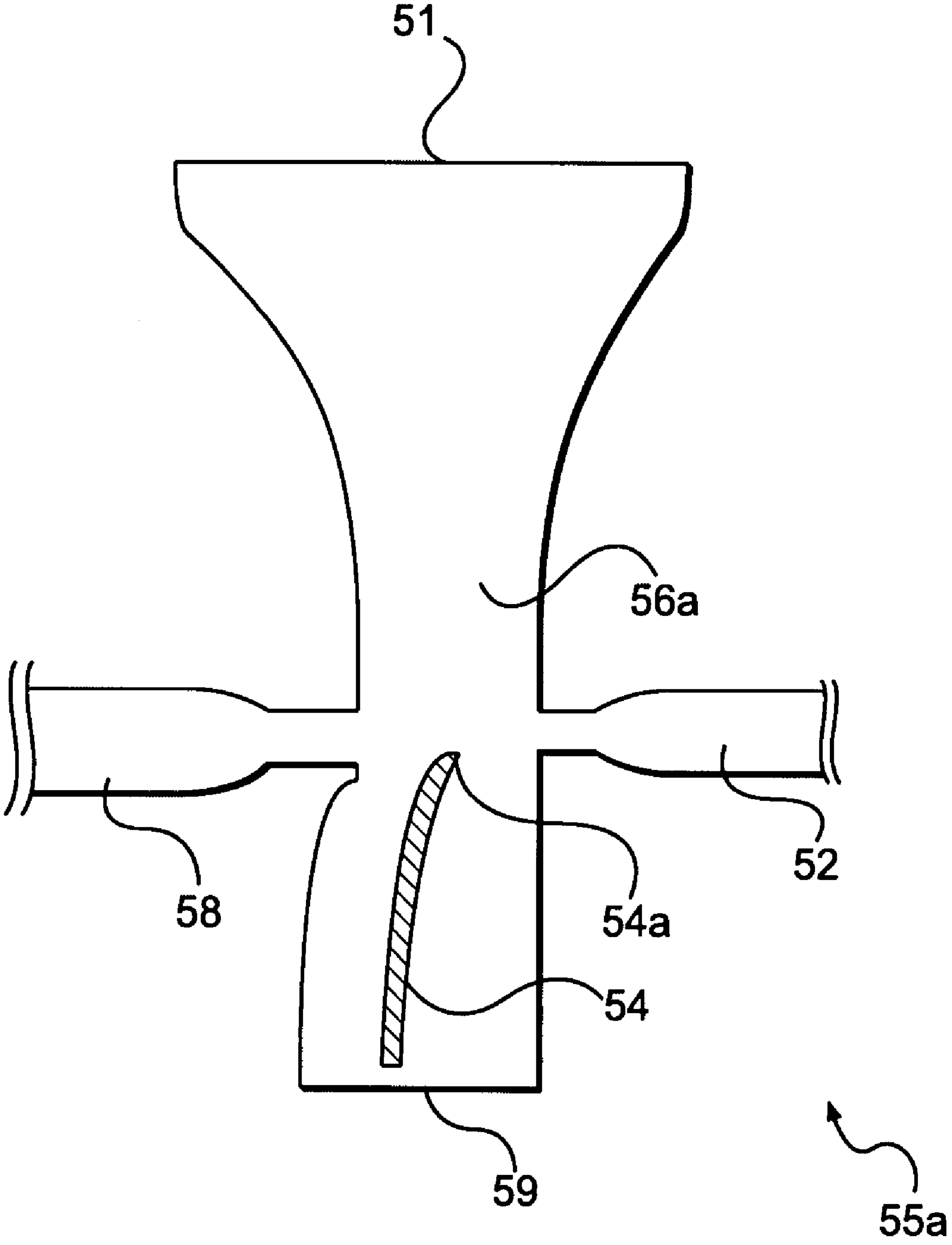
FIG. 2A is a schematic view of a venturi, according to an exemplary embodiment of the invention.

Alternatively or additionally, the venturi 55*a* may include a flow guide 54 located near its throat 56*a* between the jet inlet port 52 and the jet receiving port 58, as shown in FIG. 2A. The flow guide 54 may be made of a rigid or flexible material and have a shape of a fin with a relatively thin or shaper edge at its distal end 54*a*. Also, at least a portion of the flow guide 54 may be curved (e.g., convex shape facing the side of the jet inlet port 52). The distal end 54*a* of the flow guide 54 may be positioned slightly below the stream line of the control flow (i.e., downstream side) between the jet inlet port 52 and the jet receiving port 58. In some exemplary embodiments, the flow guide 54 may be integrally formed (e.g., molded) with the main body of the venturi 55*a*. The flow guide 54 may extend entirely across the venturi 55*a*, so as to form two separate flow passages to the outlet 59. Alternatively, the flow guide 54 may be a plate member extending from an internal surface of the venturi 55*a*.

When the patient is not inhaling, the flow guide 54 may not significantly affect the passage of the control flow across between the jet inlet port 52 and the jet receiving port 58. When the patient inhales, on the other hand, the flow guide 54 may create a sufficient drag upon the control flow passing near its distal end 54*a* (the direction of the control flow having been already altered or otherwise affected by the entrainment flow from the inlet 51 of the venturi 55*a*) to facilitate the disruption of the control flow across the venturi 55*a*. The flow guide 54 may also function as a separating wall that can block at least a portion of the control flow, thereby preventing the control flow from reaching the jet receiving port 58.

Certain nebulizer designs may allow a small amount of gas to be entrained into the venturi during a non-nebulizing mode. The gas entrained into the venturi may cause instability in the stream of control flow across the venturi, which may initiate a premature nebulization. To prevent this from occurring, a venturi may include a flow stabilizer for maintaining the stability of the control flow across the venturi during the non-nebulizing mode. The flow stabilizer may reduce the effect of the entrained flow (e.g., dampening the sensitivity) by, for example, creating a resistance to the entrained flow, compensating the impact caused by the entrained flow, and/or guiding the control flow across the venturi.

Figure 2B:
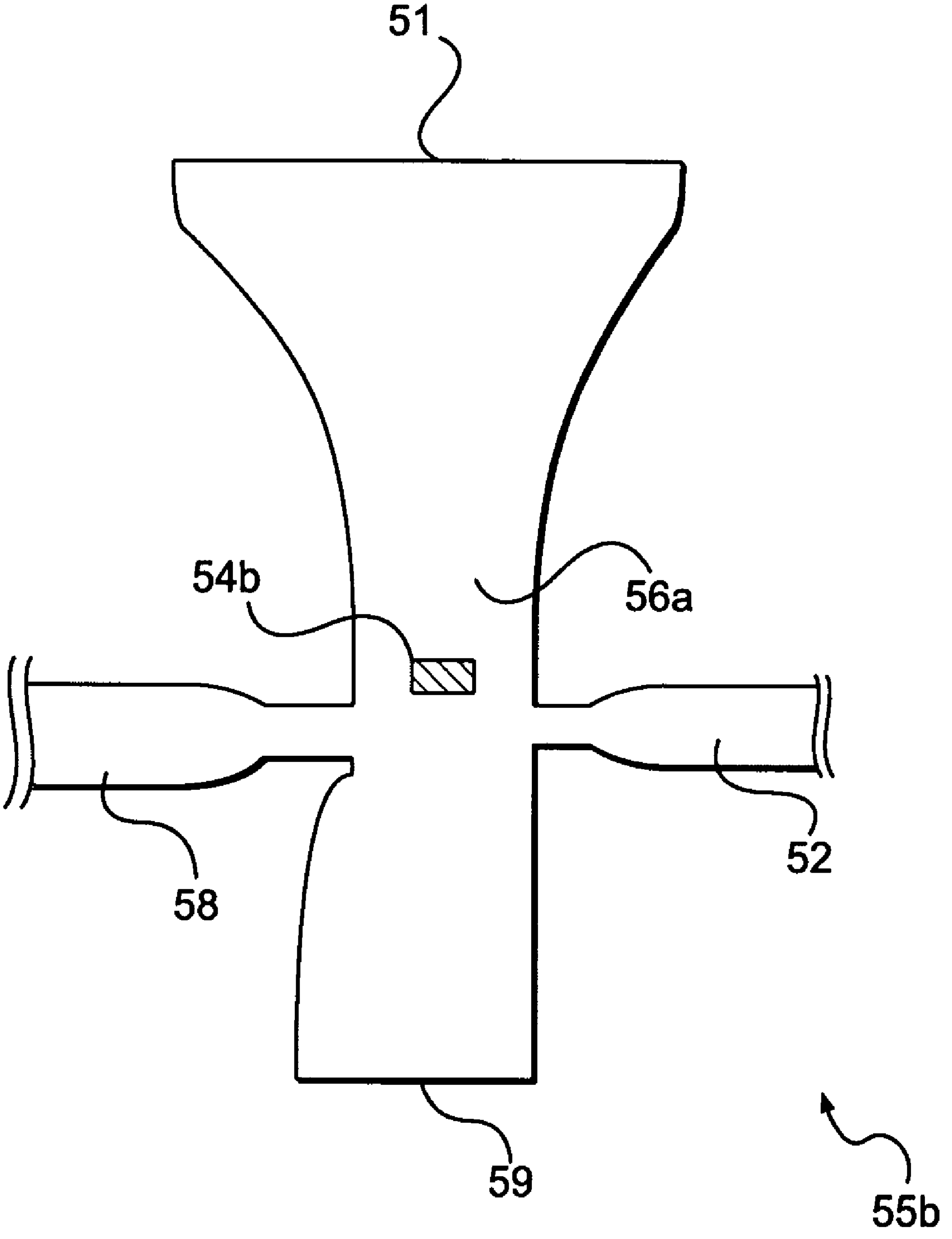
FIG. 2B is a schematic view of a venturi, according to another exemplary embodiment of the invention.
Figure 2C:
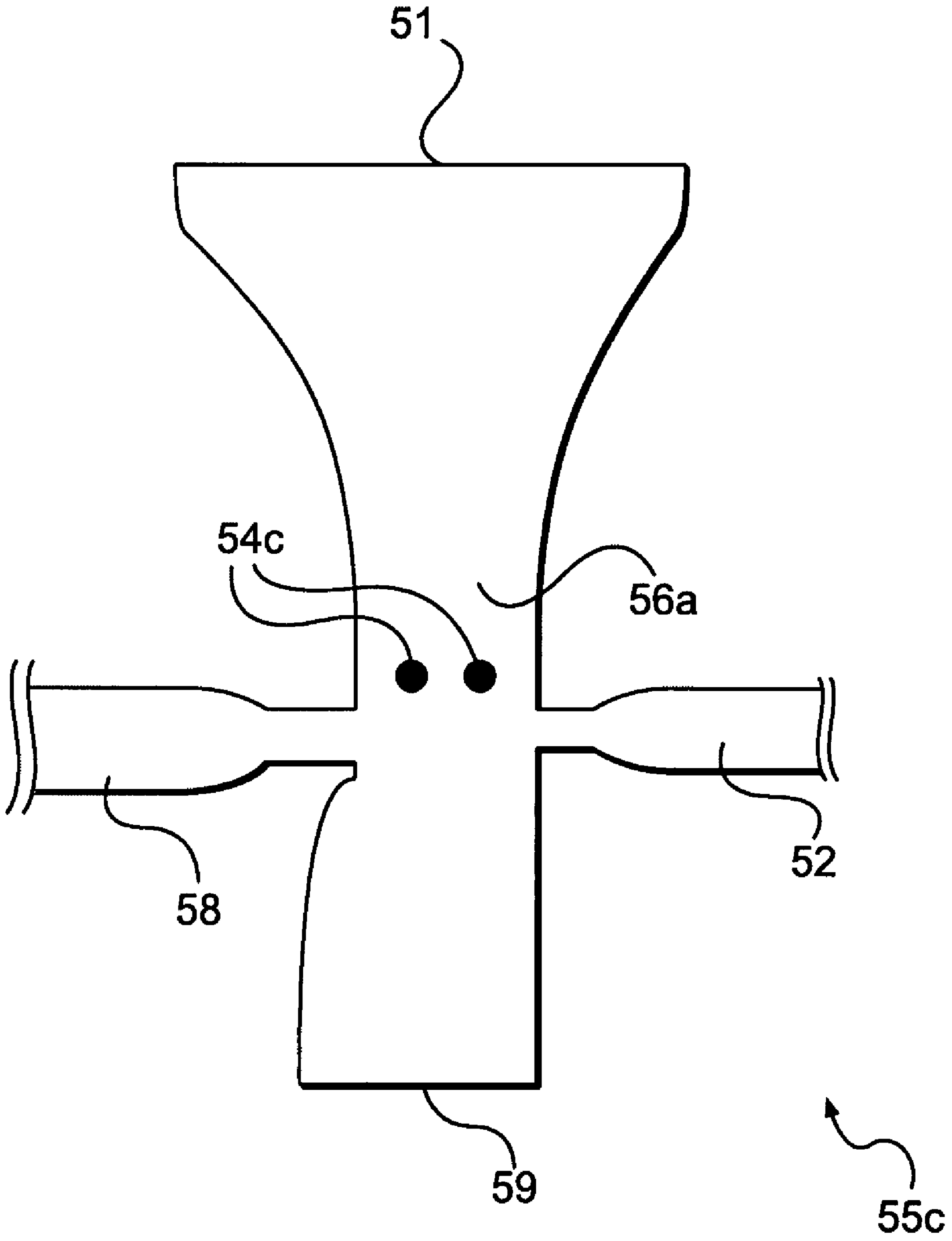
FIG. 2C is a schematic view of a venturi, according to still another exemplary embodiment of the invention.

For example, as shown in FIGS. 2B and 2C, the venturi 55*b*, 55*c* may include a flow stabilizer 54*b*, 54*c* located near the throat 56*a* between the jet inlet port 52 and the jet receiving port 58. In various exemplary embodiments, the flow stabilizers 54*b*, 54*c* may be positioned slightly above the stream line of the control flow (i.e., upstream side in the venturi 55*b*, 55*c*). The flow stabilizer 54*b*, 54*c* may have a variety of different shapes. By way of examples only, the flow stabilizer 54*b*, 54*c* may include a plate member 54*b* extending in a direction substantially parallel to the direction of the control flow, as shown in FIG. 2B, and/or one or more cylindrical protrusions 54*c* aligned in a direction substantially parallel to the direction of the control flow, as shown in FIG. 2C. It should be noted that, although the flow guide 54 and the flow stabilizer 54*b*, 54*c* are depicted separately in FIG. 2A and FIGS. 2B and 2C, respectively, a venturi may include both the flow guide 54 and the flow stabilizer 54*b*, 54*c*.

As explained above, in this nebulizing mode, the disruption of the control flow to the conduit 26 may permit the medication 30 to transport up the conduit 26 of the fluid sleeve 13 and entrain into the aerosol jet for nebulization. Once the patient inhalation stops and thereby the negative pressure diminishes or ceases, the entrainment flow through the venturi 55, 55*a* may stop. The control flow across the venturi 55, 55*a* (i.e., between the jet inlet port 52 and the jet receiving port 58) may be reestablished to permit the control flow to enter into the conduit 26 of the fluid sleeve 13, stopping the nebulization in the nebulizer 10, as shown in FIG. 1. During patient exhalation, the relief valve 45 of the outlet port 40 may open to allow the flow from the patient to vent to atmosphere, without affecting the control flow to the conduit 26. In some exemplary embodiments, the relief valve 45 may be positioned inside the nebulizer body 20 with a suitable internal flow passage communicating between the valve 45 and the outlet port 40.

Figure 4A:
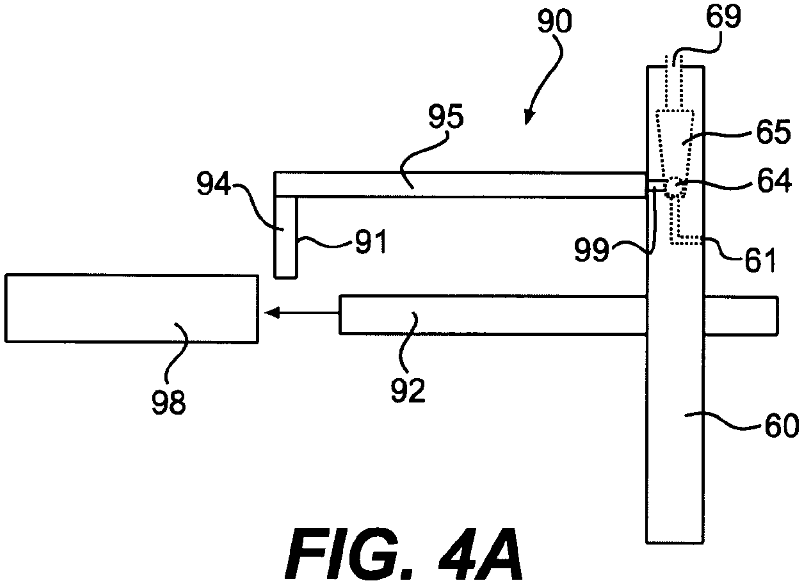
FIGS. 4A and 4B are schematic views of a control flow stopper in a non-nebulizing mode and a nebulizing mode, respectively, according to an exemplary embodiment of the invention.
Figure 4B:
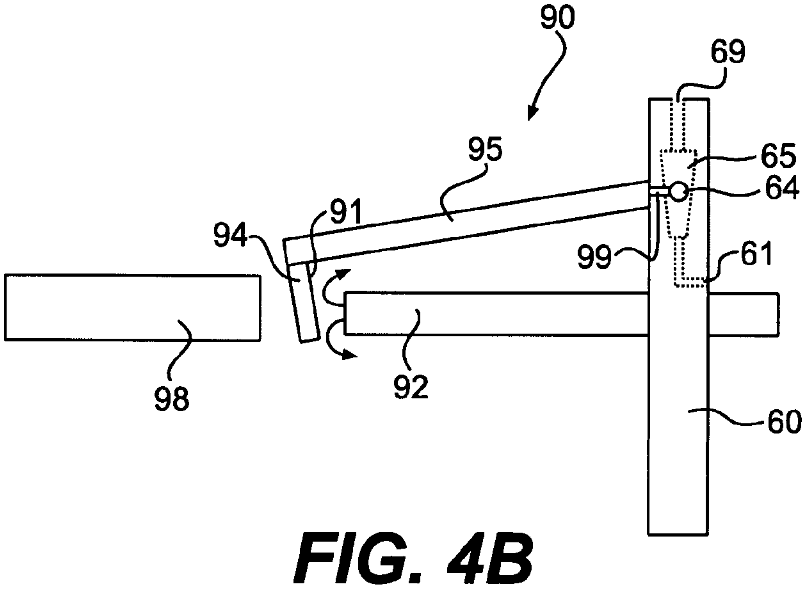

In some exemplary embodiments, instead of using the entrainment flow through the venturi 55, 55*a* to disrupt the control flow, a mechanical device that can move in response to patient inhalation may be used to disrupt the control flow. For example, as shown in FIGS. 4A and 4B, a control flow stopper 90 may be used to selectively block the jet stream of the control flow from a jet inlet port 92 to a jet receiving port 98 in response to patient inhalation. The stopper 90 may comprise a flapper arm 95 and a tab 94 attached to, or integrally formed with, a distal end portion of the flapper arm 95. When the tab 94 is positioned between the jet inlet port 92 and the jet receiving port 98, a surface 91 of the tab 94, facing the jet inlet port 92, may have a surface area large enough to completely block and/or deflect the control flow away from the jet receiving port 98. Upon patient inhalation, the flapper arm 95 may move from an open position shown in FIG. 4A (i.e., a non-nebulizing position) to a closed position shown in FIG. 4B (i.e., a nebulizing position). The flapper arm 95 may be biased in the open position (e.g., via a spring), so that, when the patient inhalation ceases, the flapper arm 95 may return to its biased open position, allowing the reestablishment of the control flow between the jet inlet port 92 and the jet receiving port 98.

To actuate the movement of the flapper arm 95 from the open position shown in FIG. 4A to the closed position shown in FIG. 4B, any suitable actuation mechanism may be used. For example, in an exemplary embodiment, the actuation mechanism may use a variable area orifice, generally used in, for example, flowmeters and hydraulic controllers. As shown in FIGS. 4A and 4B, a proximal end portion of the flapper arm 95 may be coupled (e.g., pivotally) to a suitable supporting structure 60. The supporting structure 60 may include a generally tapered flow conduit 65 having an inlet 61 in fluid communication with atmosphere and an outlet 69 in fluid communication with the outlet port 40 of the nebulizer body 20. Within the flow conduit 65, a float 64 or rotor with its outer diameter slightly less than or substantially equal to the minimum inner diameter of the flow conduit 65 may be placed, such that the clearance space between the inner wall of the flow conduit 65 and the float 64 may define a variable area orifice. A suitable mechanical, electrical, or electro-mechanical coupler 99 may be used to couple the proximal end of the flapper arm 95 to the float 64 or any other element that moves corresponding to the movement of the float 64. Upon patient inhalation, the negative pressure created at the outlet port 40 may induce a flow inside the flow conduit 65 from the inlet 61 to the outlet 69. The flow inside the flow conduit 65 may cause the float 64 to move up in the flow conduit 65, which in turn may cause the flapper arm 95 to move or pivot down to block the control flow with its tab 91. When the patient inhalation stops, the flow inside the flow conduit 65 diminishes, and the float 64 may move down to the bottom via, for example, gravity or a suitable bias member. As the float 64 moves down, the flapper arm 95 may lift up, allowing the reestablishment of the control flow between the jet inlet port 92 and the jet receiving port 98.

Figures 5, 5A, 5B:
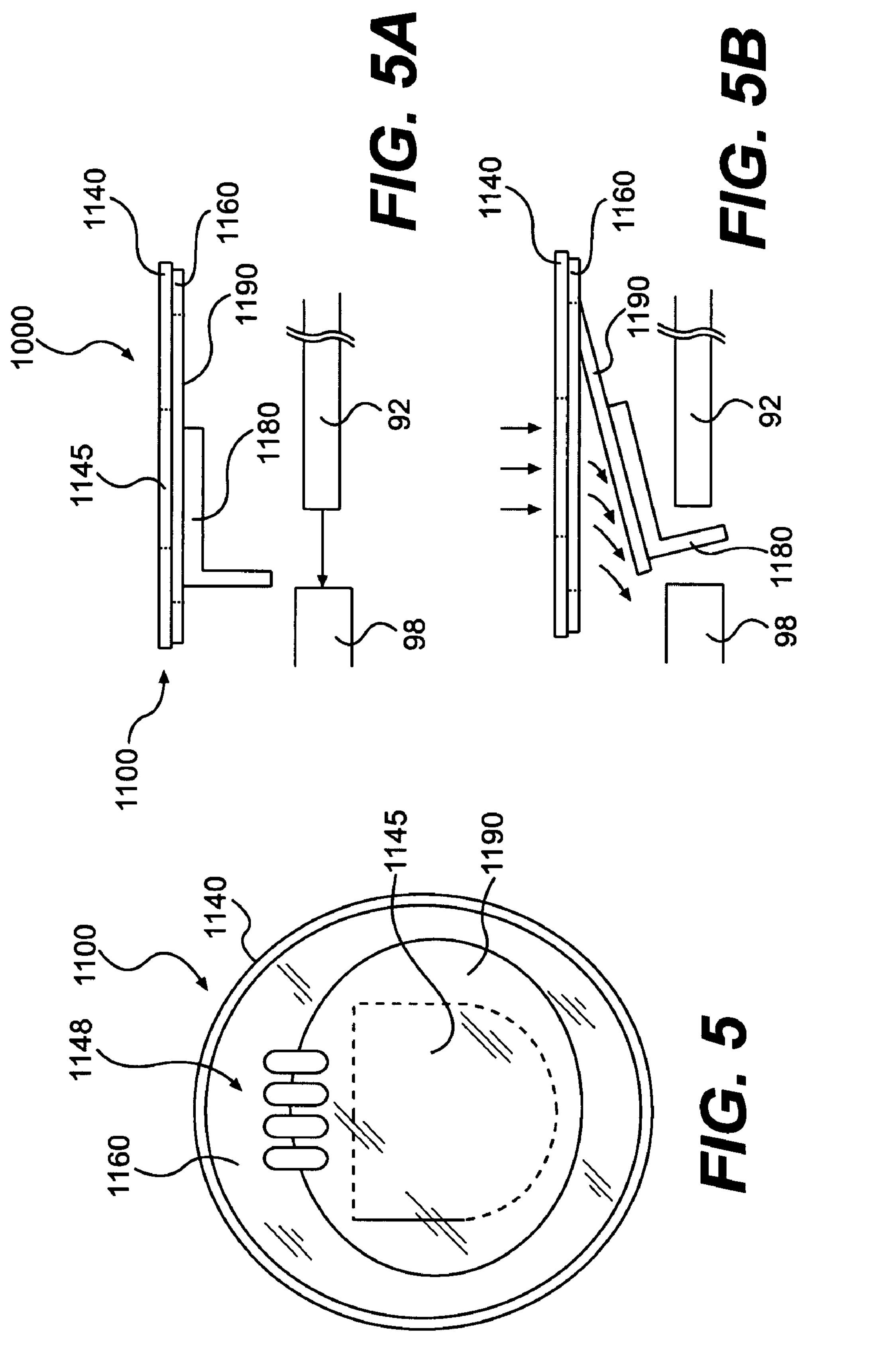
FIG. 5 is a schematic view of a flapper valve used in a control flow stopper, according to another exemplary embodiment of the invention.
FIGS. 5A and 5B are schematic views of a control flow stopper utilizing the flapper valve of FIG. 5 to switch between a non-nebulizing mode and a nebulizing mode.

Instead of, or in addition to, the variable area orifice described above, any other suitable actuation mechanisms may be used to actuate the movement of a flapper arm. For example, in one exemplary embodiment, as shown in FIGS. 5, 5A, and 5B, a flapper valve 1100 may be used to actuate the movement of a flapper arm 1180 to selectively disrupt the control flow. The flapper valve 1100 may include a first sheet 1140 having an opening 1145 and a second sheet 1160 having an opening covered with a flap 1190. The flap 1190 may be sized and configured to cover the opening 1145 of the first sheet 1140 and may be pivotally coupled to the second sheet 1160 via a pivot or bending portion 1148. When a flow enters the opening 1145 of the first sheet 1140, the flap 1190 may bend or swing open to allow the flow to pass through the opening of the second sheet 1160. The pivot member 1148 may include one or more bending beams so that the amount of bending for a given flow rate may be adjusted. The first and second sheets 1140, 1160 may be fixedly attached to one another at least at their peripheral regions, such that the flow entering the opening 1145 may pass entirely through the opening of the second sheet 1160.

As shown in FIGS. 5A and 5B, the flapper arm 1180 configured to block and/or deflect the control flow may be attached to or positioned adjacent the flap 1190, so that it can move along with the flap 1190 when the flow passes through the opening 1145. For example, upon patient inhalation, a flow through the opening 1145 may be induced, causing the flap 1190 to bend from a closed position shown in FIG. 5A (i.e., a non-nebulizing position) to an open position shown in FIG. 5B (i.e., a nebulizing position). The flapper arm 1180 may then move together with the flap 1190 to disrupt the control flow between the jet inlet port 92 and the jet receiving port 98. The flap 1190 may be biased in the closed position, so that, when the patient inhalation ceases, the flap 1190 may return to its biased closed position, allowing the reestablishment of the control flow between the jet inlet port 92 and the jet receiving port 98.

Figure 5C:
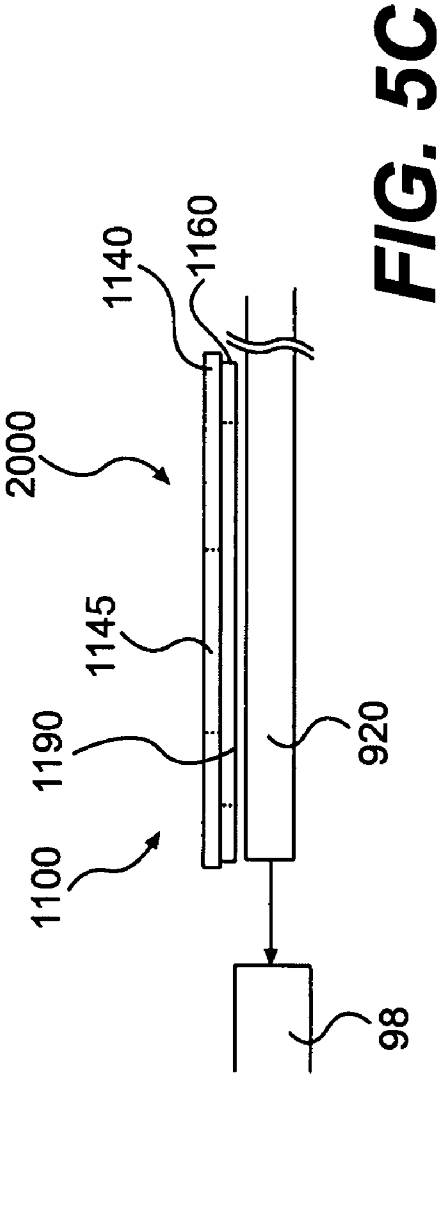
FIGS. 5C and 5D are schematic views of another control flow stopper utilizing the flapper valve of FIG. 5 to switch between a non-nebulizing mode and a nebulizing mode
Figure 5D:
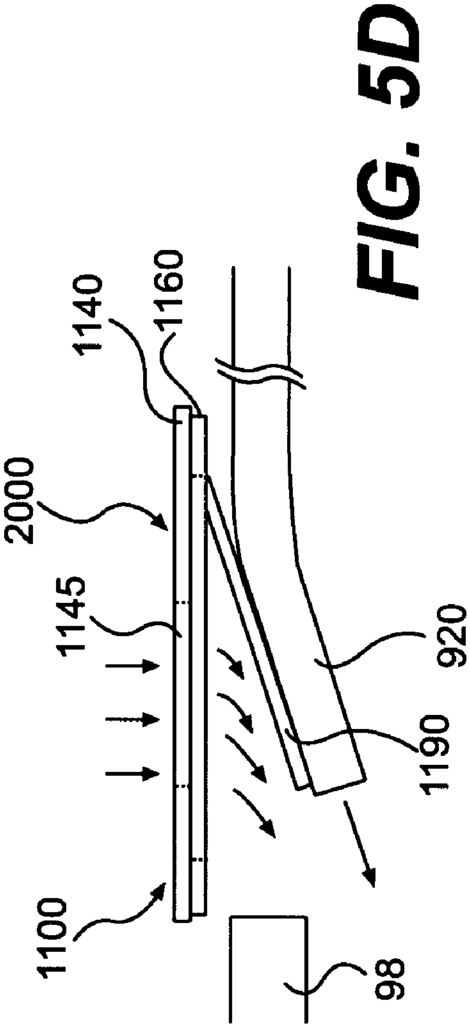

According to another exemplary embodiment, the flap 1190 may be fixedly attached to or positioned proximate a portion of the jet inlet port 920, as shown in FIGS. 5C and 5D. In this embodiment, the portion of the jet inlet port 920 may be made of a flexible material (e.g., rubber), so that when the flap 1190 bends in response to patient inhalation, the jet inlet portion 920 may be deflected to disrupt the control flow between the jet inlet port 92 and the jet receiving port 98.

Figure 6B:
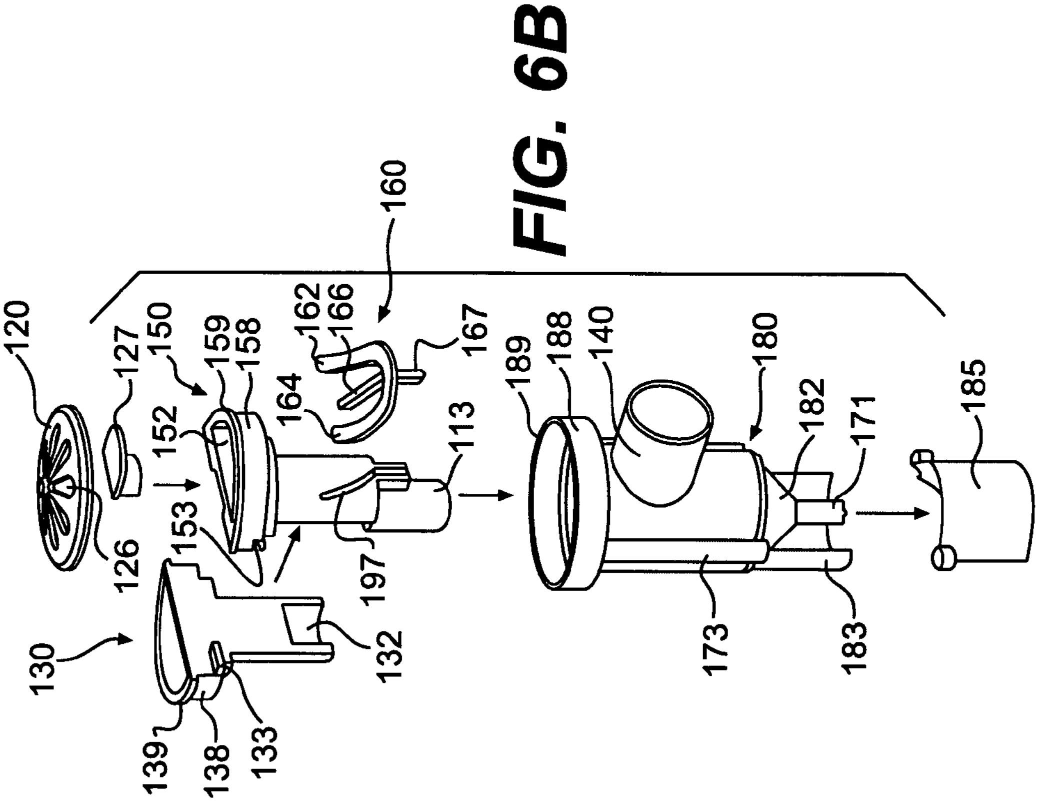
FIG. 6B is a perspective view of the nebulizer of FIG. 6A, illustrating various parts of the nebulizer.
Figure 6A:
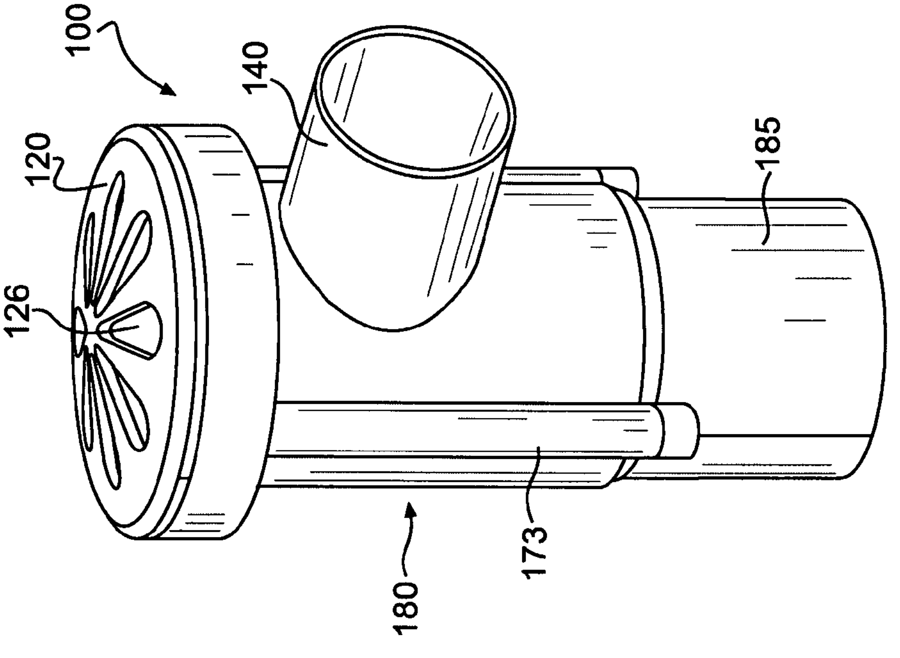
FIG. 6A is a perspective view of a nebulizer, according to another exemplary embodiment of the invention.
Figure 7:
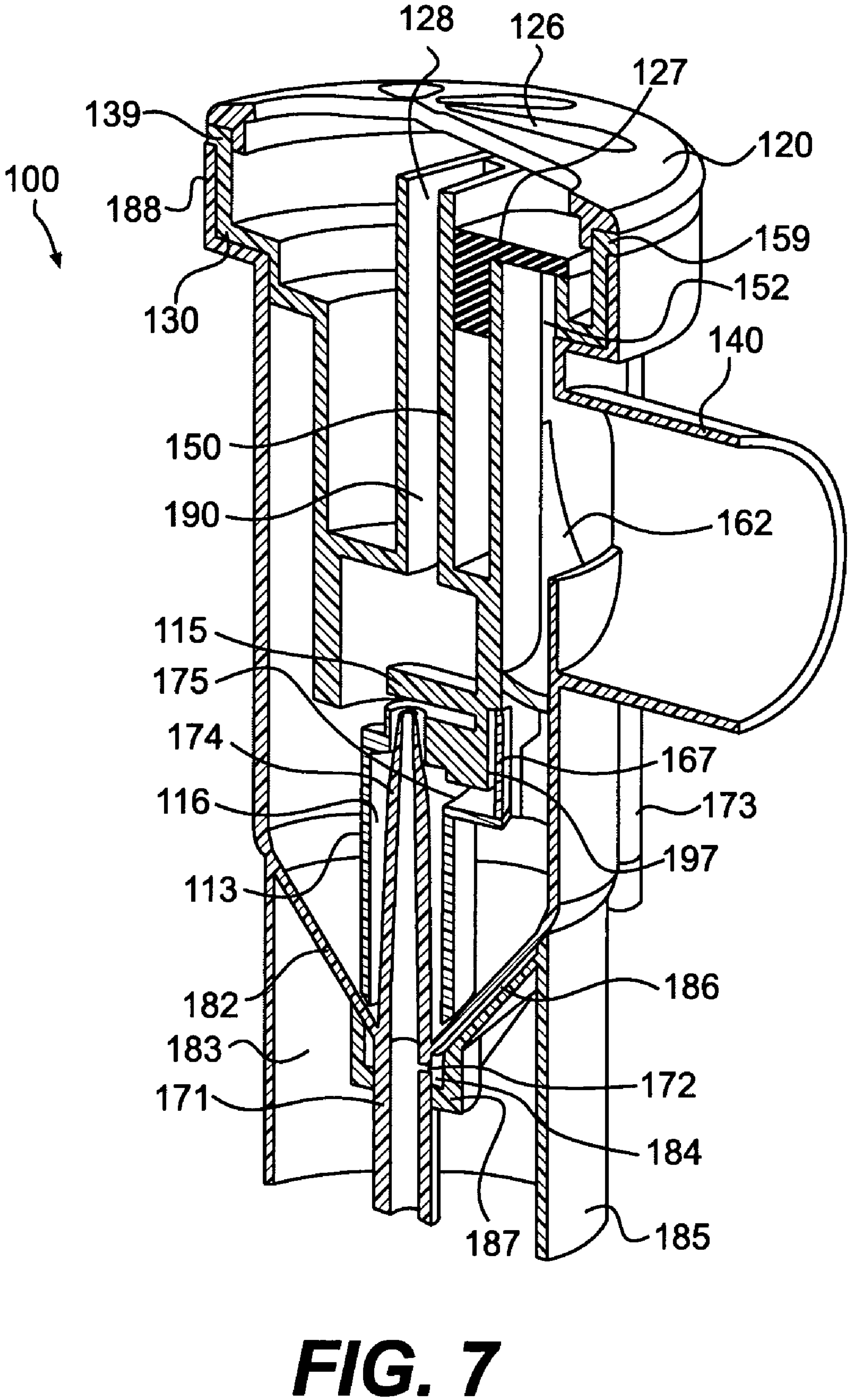
FIG. 7 is a cross-sectional, perspective view of the nebulizer of FIG. 6A.

FIGS. 6A, 6B, and 7-10 show another exemplary embodiment of a breath-actuated nebulizer 100, in which a venturi is disposed inside a nebulizer body. Referring to FIGS. 6A, 6B, and 7, the nebulizer 100 may include a nebulizer body 180, an aerosol outlet port 140 extending from the nebulizer housing 180, a two-piece internal housing 130, 150, and a lid 120. The nebulizer body 180 may comprise an upper portion 188 defining an opening for receiving the two-piece internal housing 130, 150. A lower portion of the nebulizer body 180 may define a fluid reservoir 182 for containing medication intended for nebulization. A main pressurized gas line 171 and a nozzle 174 for generating an aerosol jet may extend through the center of the fluid reservoir 182, as shown in FIG. 7. In an exemplary embodiment, the gas line 171 and the nozzle 174 may be integrally formed (e.g., via injection molding) with the fluid reservoir 182.

The nebulizer 100 may also include a flow director 160 having a pair of baffles 162, 164, which may be removably attached to a portion of the internal housing 130, 150. The flow director 160 may provide an exit path in a space between the external surface of the internal housing 130, 150 and the inner surface of the body 180 to guide the generated aerosol to the outlet port 140. At the same time, the flow director 160 may create a tortuous path for the generated aerosol, which may function as a filtering mechanism for filtering out relatively larger aerosol particles before exiting to the patient. For example, due to the flow resistance created by the flow director 160, the larger aerosol particles may condense on the surface of the baffles 162, 164 and/or may flow back to the fluid reservoir 182. The flow director 160 may also include sealing extensions 166, 167 configured to mate with a control channel 197 of the internal housing 150, which will be described later in detail.

Figure 9:
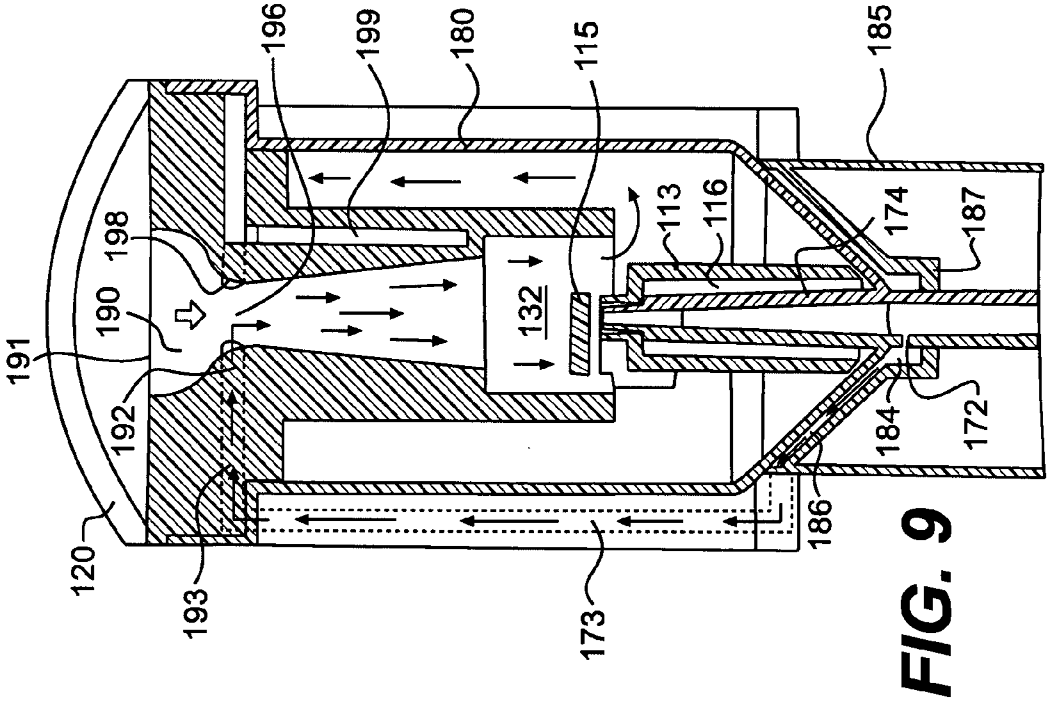
FIGS. 8 and 9 are cross-sectional views of the nebulizer of FIG. 6A, illustrating control flow directions during a non-nebulizing mode and a nebulizing mode, respectively.
Figure 8:
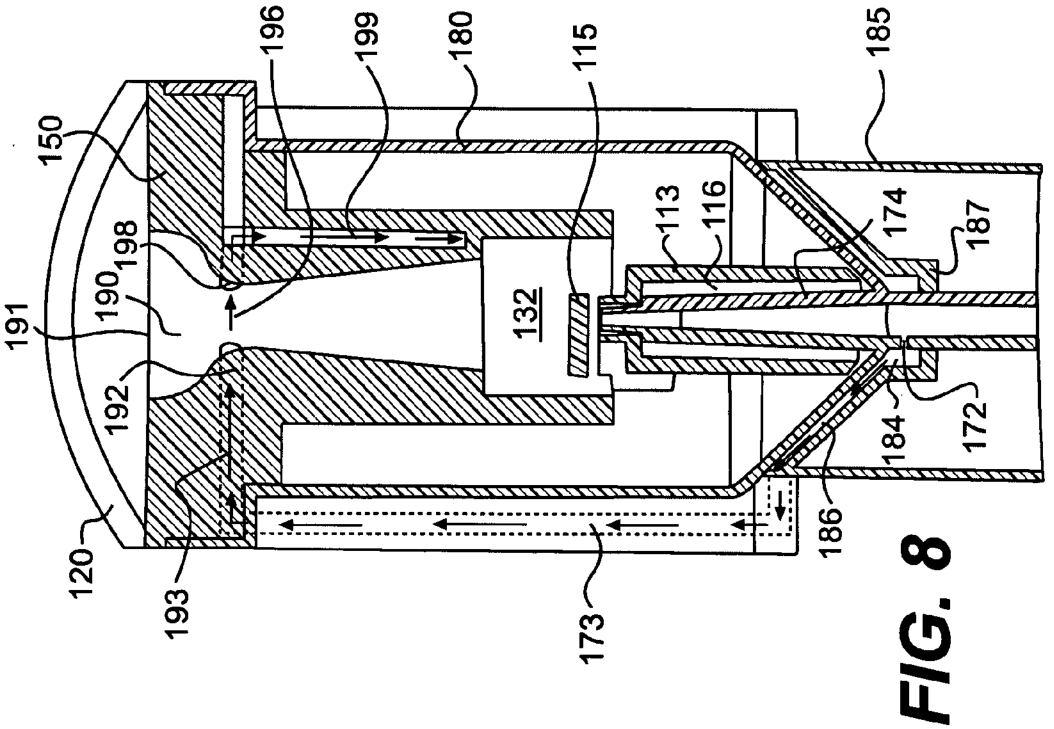

The nebulizer body 180 may also include a first skirt 183 surrounding a portion (e.g., half) of the fluid reservoir 182 and a second skirt 185 removably attached to the body 180 and/or the first skirt 183. The first skirt 183 and the second skirt 185 may form an annular sleeve completely surrounding the fluid reservoir 182. As best shown in FIG. 7, the second skirt 185 may include a control flow manifold 187 configured to guide the control flow from an opening 172 of the gas line 171 to a side conduit 173 of the nebulizer body 180. The opening 172 may create a pressure drop in the gas line 171 to draw a low-flow (e.g., approximately 1-5 lpm), low-pressure (e.g., approximately 50-140 cm water) control flow out of the gas line 171. The flow area and/or the geometry of the opening 172 may be varied to draw a desired amount of the control flow. The control flow manifold 187 may define an internal space 184 in fluid communication with the opening 172 and a flow passage 186 (e.g., a groove or conduit) connecting the space 184 to the side conduit 173. The side conduit 173 may extend vertically upward along the height of the nebulizer body 180 and connect to an inlet flow path 193 of the internal housing 130, 150, as best shown in FIGS. 8 and 9. Suitable sealing members may be used to seal various flow passages and connections.

Although FIGS. 6B and 7 depict the second skirt 185 as being a separate piece, many different arrangements may be possible. For example, in one exemplary embodiment, the second skirt 185 and/or the control flow manifold 187 may be integrally formed with the first skirt 183. In another exemplary embodiment, the first and second skirts 183, 185 may be integrally formed with one another, while the control flow manifold 187 may be separately attached to, or integrally formed with, the reservoir 182. In still another exemplary embodiment, the nebulizer 100 may not include any of the first and second skirts 183, 185, while the control flow manifold 187 may be removably or integrally attached to the reservoir 182.

Referring to FIGS. 6B and 7, the two-piece internal housing 130, 150 may comprise a first piece 130 and a second piece 150, which may be configured to engage one another via a protrusion 133 and a corresponding groove 153. Any other suitable engagement mechanism known in the art may be used additionally or alternatively. When engaged, the first and second pieces 130, 150 may form an internal space 190 therebetween, as best shown in FIG. 7. In various exemplary embodiments, the internal space 190 may define a venturi 190, operational characteristics of which may be similar to the venturi 55, 55*a* described above with reference to FIGS. 1, 2, and 2A. In an alternative embodiment, the first and second pieces 130, 150 may be integrally formed as a single piece.

Each of the first and second pieces 130, 150 may include a stepped portion 138, 158 and a flange 139, 159 configured to engage a stepped portion and a rim 189 of the upper portion 188, as shown in FIGS. 6B and 7, so that the internal housing 130, 150 can be securely positioned inside the nebulizer body 180. The nebulizer 100 may also include a lid 120 having one or more openings 126. The lid 120 may include a suitable valve or pressure regulator to open and close the openings 126 in response to patient's breath. The lid 120 may be coupled to the top of the internal housing 130, 150 via a suitable coupling mechanism, such as, for example, a snap-fastening or threading mechanism.

The second piece 150, located closer to the outlet port 140, may define an exhalation opening 152 through which an exhalation flow from the patient during patient exhalation may be vented to atmosphere. In order to ensure that the exhalation opening 152 opens only during the patient exhalation, a relief valve 127 (e.g., a resilient check valve) may be placed over the opening 152, as shown in FIG. 7. When the patient is inhaling through the outlet port 140, the negative pressure inside the nebulizer body 180 may pull the relief valve 127 against the top of the second piece 150 and thereby cause the relief valve 127 to remain seated over the second piece 150 and close the exhalation opening 152. When the patient exhales through the outlet port 140, at least a portion of the relief valve 127 may lift up or bend to allow the exhalation flow from the patient to vent out to atmosphere through the exhalation opening 152 and the openings 126 of the lid 120.

As best shown in FIGS. 6B and 7, the nebulizer 100 may include a diverter 115 and a fluid sleeve 113 integrally formed with the second piece 150. In some alternative exemplary embodiments, the diverter 115 and/or the fluid sleeve 113 may be removably attached to the second piece 150 or integrally formed with the nebulizer body 180. The diverter 115 may have a substantially flat plate extending laterally from a side wall of the second piece 150. The fluid sleeve 113 may comprise an elongated cylindrical body having an opening at each end. During assembly, the fluid sleeve 113 may slide over the nozzle 174. The opening at the top of the fluid sleeve 113 may receive the tip of the nozzle 174, and the nozzle 174 may face the diverter 115 in a direction substantially perpendicular to a surface of the diverter 115. The annular space between the fluid sleeve 113 and the nozzle 174 may define a fluid conduit 116 for transporting the medication contained in the fluid reservoir 182 to the aerosol jet proximate the divertor 115 for nebulization. When the fluid sleeve 113 is placed over the nozzle 174, the bottom portion of the fluid sleeve 113 may form an opening, gap, or groove with the interior surface of the reservoir 182 to provide a fluid communication between the reservoir 182 and the fluid conduit 116.

As mentioned above, the first and second pieces 130, 150 may form an internal space 190 therebetween, which may have a shape of a venturi 190. In an alternative embodiment, either the first piece 130 or the second piece 150 alone may form the venturi 190. In another alternative embodiment, the first and second pieces 130, 150 may form a single piece defining the venturi 190. As best shown in FIGS. 8 and 9, the venturi 190 may include an inlet 191 in fluid communication with atmosphere (e.g., via the openings 126 of the lid 120) and an outlet communicating with an internal space 132 proximate the diverter 115. During patient inhalation, atmospheric gas may be entrained into the venturi 190 through the inlet 191 and may enter the internal space 132, which may carry the nebulized medication to the patient via the outlet port 140.

As shown in FIGS. 6B through 9, the second piece 150 may define a control channel for delivery of the control flow from the side conduit 173 to the fluid conduit 116 of the fluid sleeve 113. The control channel may include a jet inlet path 193, a jet outlet path 199, and a control conduit 197. The jet inlet path 193 may be configured to receive the control flow from the side conduit 173 and direct the control flow to the venturi 190 via a jet inlet port 192. As shown in FIG. 8, when the patient is not inhaling, the control flow exiting the jet inlet port 192 may form a jet stream to pass across the venturi 190 and enter into a jet receiving port 198 positioned substantially opposite the jet inlet port 192. The jet inlet port 192 and the jet receiving port 198 may be aligned in a direction substantially perpendicular to a longitudinal axis of the venturi 190. The opening area of the jet receiving port 198 may be greater than the opening area of the jet inlet port 192. In some exemplary embodiments, the jet inlet port 192 and the jet receiving port 198 may be positioned proximate a throat region 196 of the venturi 190.

The control flow entering the jet receiving port 198 may travel down through the jet outlet path 199, as shown in FIG. 8, and may enter the control conduit 197. The control conduit 197 may be formed by a groove formed on an external surface of the second piece 150 and the sealing extensions 166, 167 of the flow director 160 that may cover the groove. As best shown in FIG. 7, the control conduit 197 may connect to the exit port 175 defined by an opening in the fluid sleeve 113. When the control flow enters the fluid conduit 116 via the exit port 175, the control flow may interrupt the uptake of the medication into the fluid conduit 116, thereby interrupting nebulization of the medication. Upon patient inhalation, as shown in FIG. 9, atmospheric gas may enter the venturi 190 through the inlet 191 and disrupt the stream of the control flow across the venturi 190. As a result, the control flow may no longer enter the fluid conduit 116. Interrupting the control flow to the fluid conduit 116 may allow the medication contained in the reservoir 182 to transport into the fluid conduit 116 and entrain into the aerosol jet for nebulization. The configuration and operational characteristics of the venturi 190 are similar to the embodiment shown in FIGS. 1 and 2 and, therefore, a detailed description of the venturi 190 is omitted. Also, the venturi 190 may be replaced or supplemented by any of the control flow stoppers 90, 1000, 2000 shown in FIGS. 4A and 4B, FIGS. 5A and 5B, and FIGS. 5C and 5D to selectively disrupt the control flow.

Figure 10:
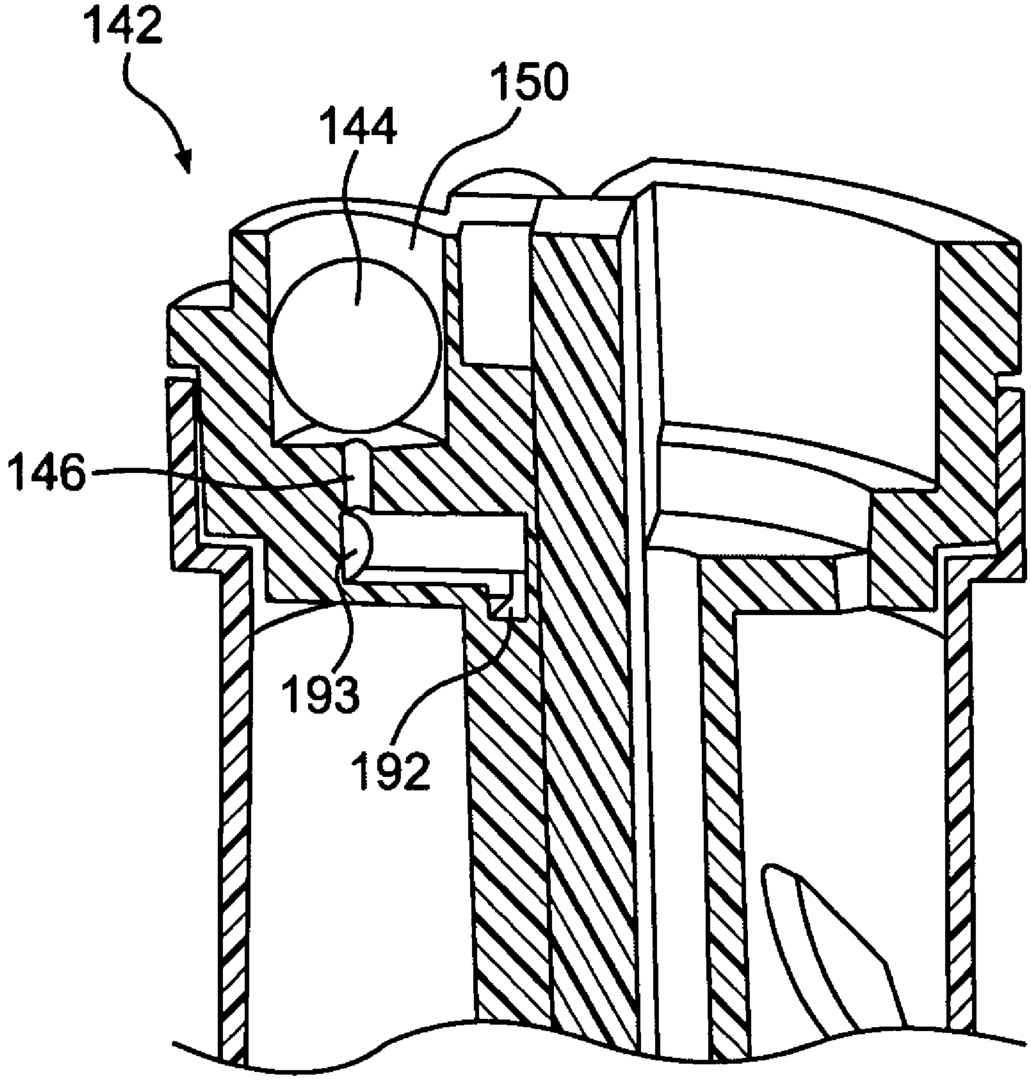
FIG. 10 is a partial cross-sectional, perspective view of the nebulizer of FIG. 6A, illustrating an exemplary control flow regulator.

The nebulizer 100 may also include a control flow regulator 142 configured to maintain the control flow within a certain flow rate range. As shown in FIG. 10, the control flow regulator 142 may comprise a weighted float 144 disposed over a fixed orifice 146. The orifice 146 may be in fluid communication with the jet inlet path 193 adjacent the jet inlet port 192. When the flow rate of the control flow exceeds a specified threshold value, the float 144 may be lifted to open the orifice 146 and vent excess control flow out to atmosphere to maintain the control flow within a desired range. While the control flow regulator 142 is located at the jet inlet path 193 in the embodiment shown in FIG. 10, the flow regulator 142 may be positioned at any other location in the control channel for the control flow, including the control flow manifold 187 and the side conduit 173.

FIGS. 11 through 20 show another exemplary embodiment of a breath-actuated nebulizer 200. The nebulizer 200 may include a generally cylindrical body 280 and a cap 220 configured to engage with a top portion of the body 280 via a suitable engagement mechanism, such as, for example, a snap-fastening or threading mechanism. The body 280 may open to atmosphere at its bottom end to provide an entrainment port for the entrainment flow from atmosphere during patient inhalation. The nebulizer 200 may also include an aerosol outlet port 240 extending from the cap 220 to deliver nebulized medication to a patient.

Figure 13:
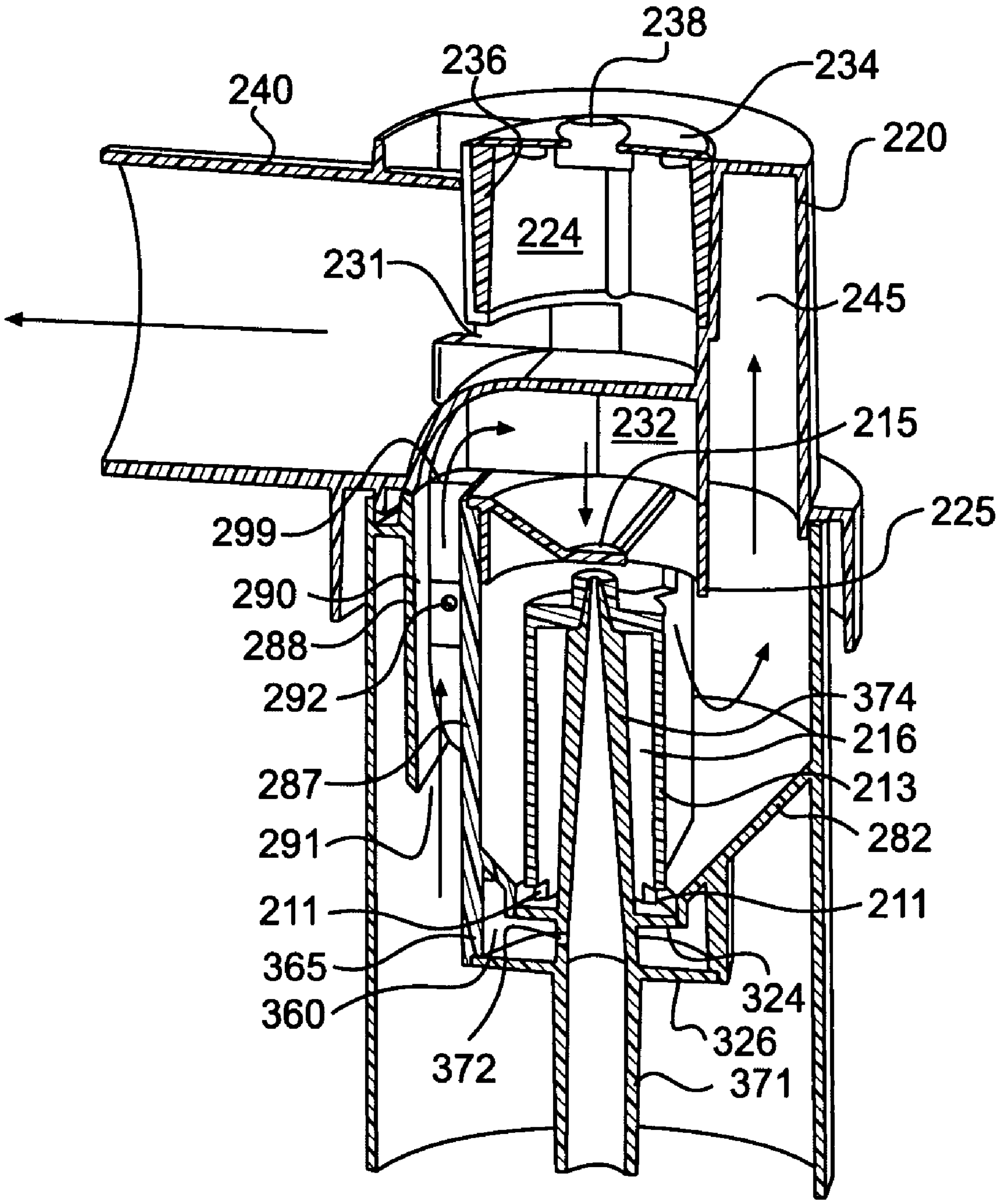
FIGS. 13 and 14 are cross-sectional, perspective views of the nebulizer of FIG. 11, illustrating flow directions within the nebulizer during patient inhalation and exhalation, respectively.
Figure 14:
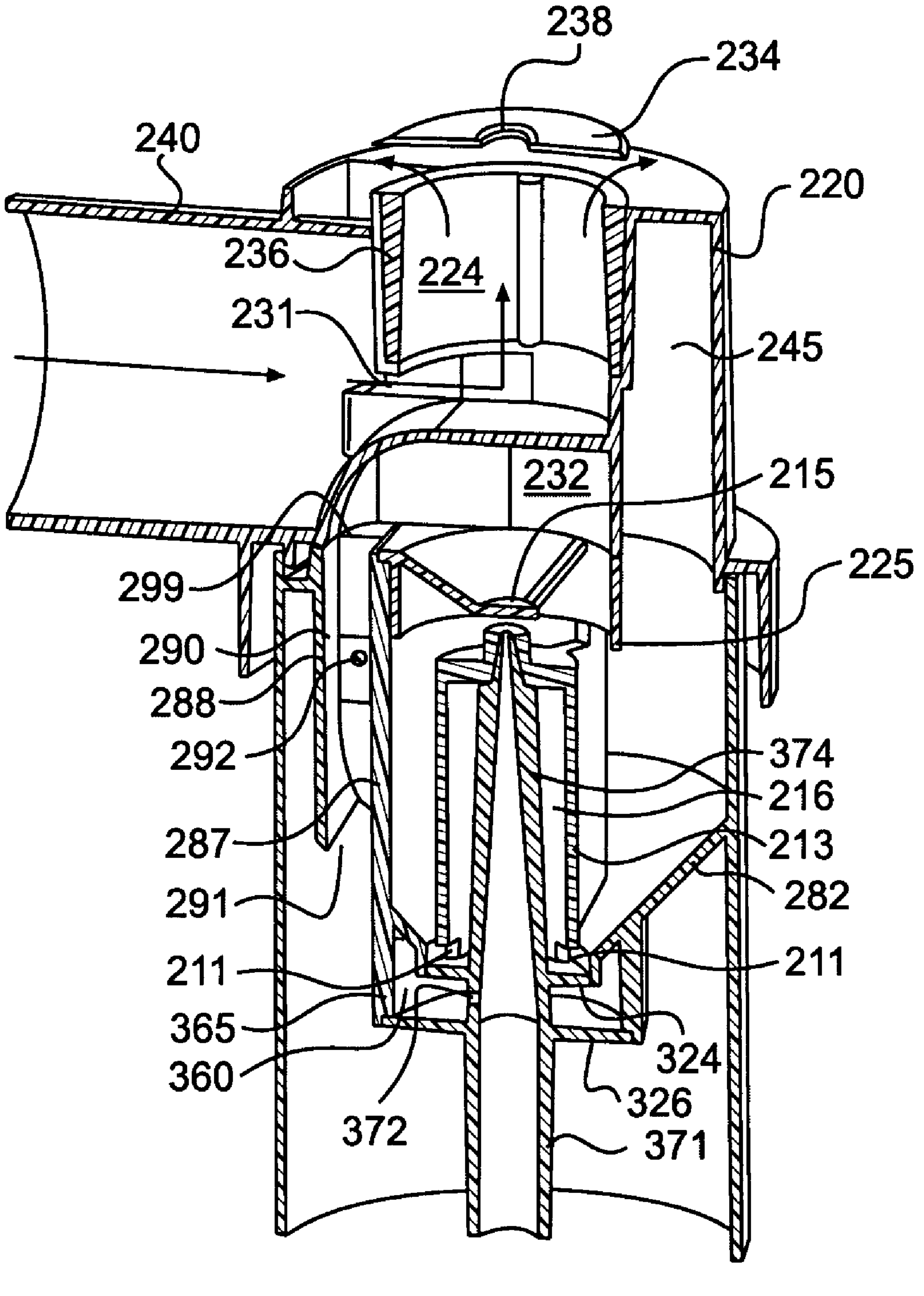
Figure 15:
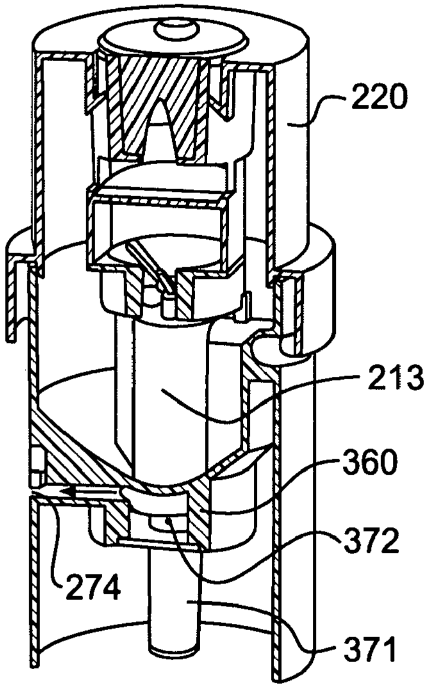
FIGS. 15-17 are cross-sectional, perspective views of the nebulizer of FIG. 11, illustrating control flow directions during a non-nebulizing mode.

Within the body 280, as best shown in FIGS. 13 and 14, the nebulizer 200 may include a medication reservoir 282 for containing medication intended for nebulization. Inside the reservoir 282, a fluid sleeve 213 having one or more openings 211 in fluid communication with the reservoir 282 may be disposed integrally with, or separated from, the reservoir 282. The fluid sleeve 213 may be configured to receive a nozzle 374 for generating an aerosol jet. An annular space between the fluid sleeve 213 and the nozzle 374 may define a fluid conduit 216 for transporting the medication contained in the fluid reservoir 282 proximate the aerosol jet for nebulization.

In some exemplary embodiments, the nozzle 374 and a main pressurized gas line 371 for supplying pressured gas to the nozzle 374 may constitute a separate piece removable from the fluid sleeve 213. For example, the fluid sleeve 213 and the reservoir 282 may define bottom openings, through which the nozzle 374 may be inserted. To seal the opening of the fluid sleeve 213, the nozzle 374 may include an annular flange 324 that may constitute a portion of the reservoir 282. In an alternative embodiment, the fluid sleeve 213 and the nozzle 374 may be integrally formed as a single piece.

Figure 11:
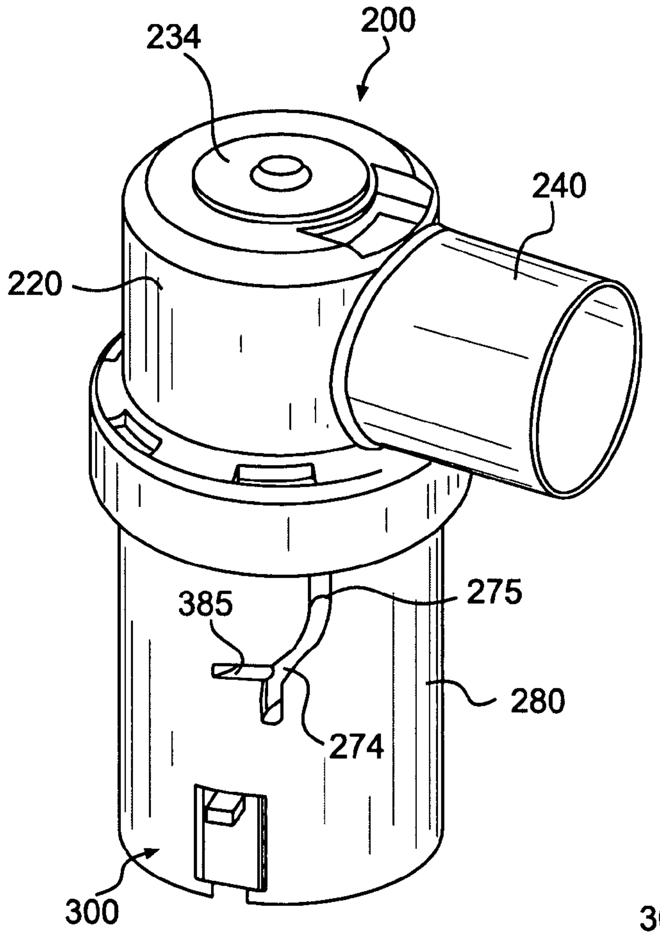
FIG. 11 is a perspective view of a nebulizer, according to another exemplary embodiment of the invention.

The nozzle 374 may also include an opening 372 below the annular flange 324 to draw the control flow therefrom. A skirt 365 extending from an external surface of the reservoir 282 and a second annular flange 326 extending laterally from the nozzle 374 may define a control flow manifold 360 for directing the control flow drawn from the opening 372 to a side wall conduit 274. The side conduit 274 formed on an external surface of the body 280, as best shown in FIG. 11, may extend upwardly to connect to an inlet flow path 275 of a venturi 290, as will be explained further herein. A suitable sealing member may be provided to cover the side conduit 274. Where the angular position of the inlet of the inlet flow path 275 with respect to a longitudinal axis of the body 280 is different from that of the exit of the control flow manifold 360, a portion of the side conduit 274 may be curved to connect the control flow manifold 360 to the inlet flow path 275. The opening 372 in the nozzle 374 or the gas line 371 may be similar to the opening 172 of the embodiment shown in FIGS. 6B through 9 and, therefore, a detailed description is omitted herein.

Figure 12:
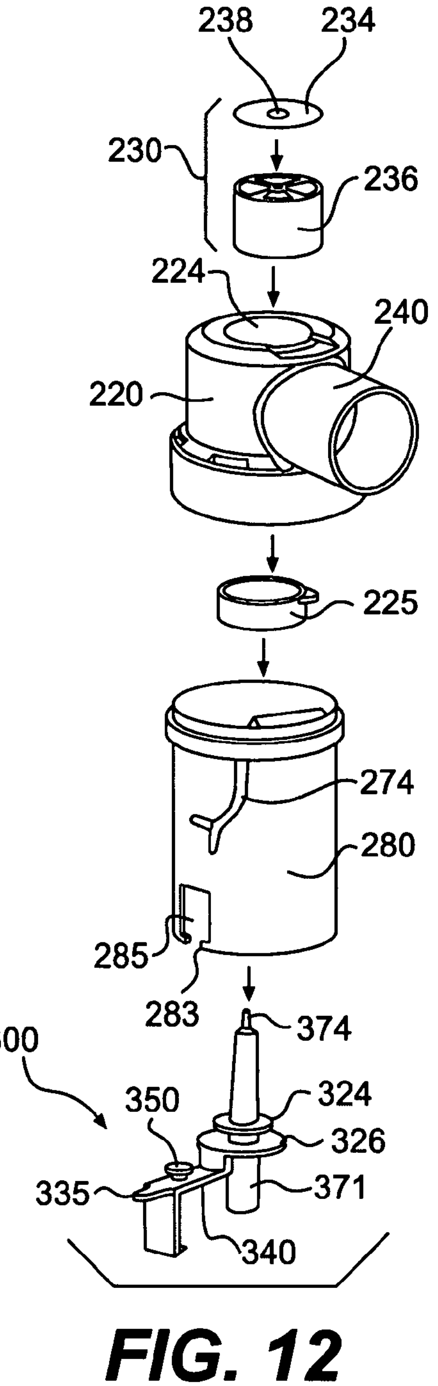
FIG. 12 is a perspective view of the nebulizer of FIG. 11, illustrating various parts of the nebulizer.

The nebulizer 200 may include a diverter 225 to which the aerosol jet from the nozzle 374 may be directed for nebulization. The diverter 225 may comprise a substantially flat plate portion 215 and a ring portion for supporting, at least partially, the flat plate portion 215. As shown in FIG. 12, the diverter 225 may be removably positioned above the nozzle 374 with the flat plate portion 215 positioned directly above the tip of the nozzle 374. Although the diverter 225 may be removably placed relative to the nozzle 374, when assembled, the diverter 225 and the flat plate portion 215 may remain in a fixed position relative to the nozzle 374.

The nebulizer 200 may also include a venturi 290 disposed in a space between an outer skirt 288 and a side baffle 287 defining a portion of the reservoir 282. The venturi 290 may include an inlet 291 facing the bottom opening of the body 280 to communicate with atmosphere and an outlet 299 communicating with an internal space 232 proximate the diverter 215. During patient inhalation, as shown in FIG. 13, atmospheric gas may be entrained into the venturi 290 through the inlet 291, exit the venturi 290 through the outlet 299, and enter the internal space 232 to mix with the nebulized medication. The entrained gas mixed with the nebulized medication in the internal space 232 may flow to the outlet port 240 via an exit passage 245 defined inside the cap 240. The operational characteristics of the venturi 290 in connection with the control flow will be explained in more detail later with reference to FIGS. 15-18.

The cap 220 may also define a venting passage 224 that may provide a flow passage between the outlet port 240 and atmosphere during patient exhalation. An exhalation valve assembly 230 may be disposed in the venting passage 224 to permit flow through the venting passage 224 only during the patient exhalation. In an exemplary embodiment, as best shown in FIG. 12, the valve assembly 230 may include a venting chimney 236 defining one or more openings therethrough and a plate member 234 configured to open and close the openings of the chimney 236. The plate member 234 may include a central opening 238 configured to mate with a button located on the top of the chimney 236. The plate member 234 may be movable relative to the chimney 236 such that, when the patient exhales through the outlet port 240, the plate member 234 moves up relative to the chimney 236 to open the openings of the chimney 236 and thereby permit exhalation flow from the patient to vent out to atmosphere, as shown in FIG. 14. When the patient exhalation stops or during the patient inhalation, the plate member 234 may move down to cover the openings of the chimney 236 to prevent any flow therethrough. In some exemplary embodiments, the plate member 234 may be attached to a biasing member (e.g., a spring) to maintain the venting passage 224 in a closed position until a flow corresponding to the patient exhalation exists in the venting passage 224. While the present disclosure describes a particular embodiment of the exhalation valve assembly, any other suitable valve mechanism known in the art may be used alternatively or additionally. For example, in addition to, or in alternative to, the valve assembly 230, the venting passage 224 may include a check valve (e.g., a resilient diaphragm) at an orifice 231 communicating with the outlet port 240 to permit a flow only from the outlet port 240 to the venting passage 224.

Figure 16:
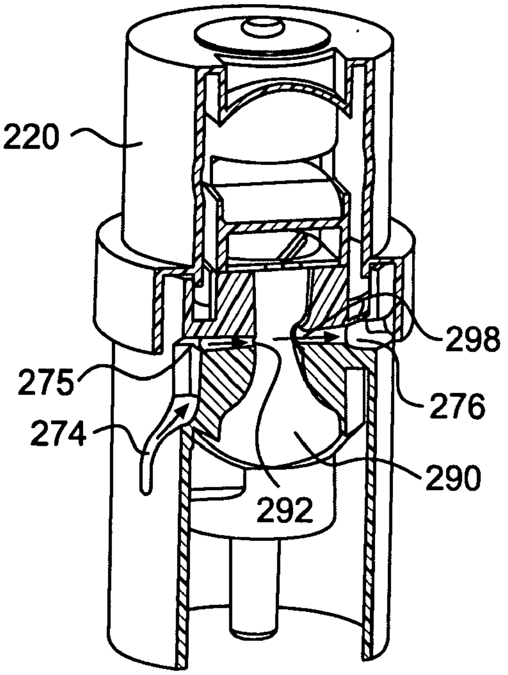
Figure 17:
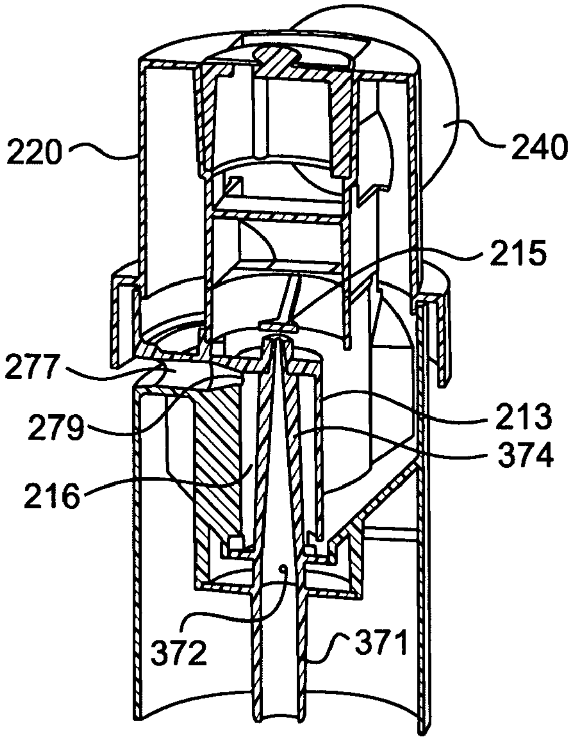

Referring to FIGS. 15-18, the control path for delivery of the control flow from the control manifold 360 to the fluid conduit 216 of the fluid sleeve 213 will be described. As discussed above, the control flow manifold 360 may be configured to direct the control flow drawn from the opening 372 in the main pressurized gas line 371 to the side conduit 274. The side conduit 274 may extend upwardly to connect to a jet inlet path 275. The jet inlet path 275 may direct the control flow received from the side conduit 274 to a jet inlet port 292 proximate the venturi 290. As shown in FIG. 16, when the patient is not inhaling, the control flow exiting the jet inlet port 292 may form a jet stream to pass across the venturi 290 and enter into a jet receiving port 298 positioned substantially opposite the jet inlet port 292. The jet inlet port 292 and the jet receiving port 298 may be aligned in a direction substantially perpendicular to a longitudinal axis of the venturi 290. The control flow entering the jet receiving port 298 may enter the jet outlet path 276 configured to direct the control flow to a control conduit 277. The control conduit 277 may be defined by a groove or conduit formed on an external surface of the body 280, which may partially extend circumferentially around the body 280 (e.g., approximately 90°), as shown in FIGS. 16 and 17. The control conduit 277 may connect to an exit port 279 that communicates with the fluid conduit 216 of the fluid sleeve 213. The control flow entering the fluid conduit 216 may disrupt the entrainment of the medication into the fluid conduit 216, thereby disrupting or preventing nebulization in the nebulizer 200.

Figure 18:
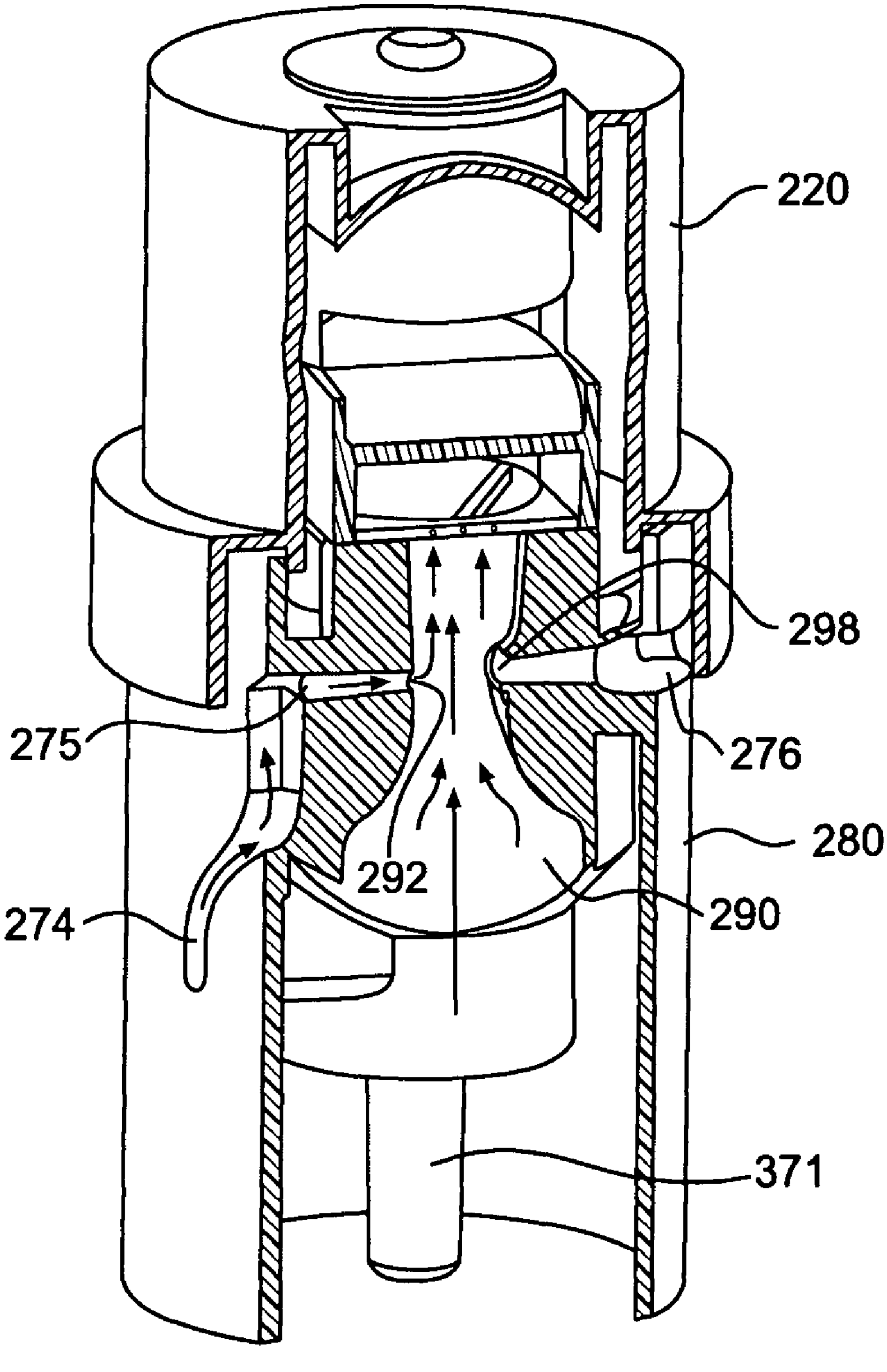
FIG. 18 is a cross-sectional, perspective view of the nebulizer of FIG. 11, illustrating control flow directions during a nebulizing mode.

Upon patient inhalation, as shown in FIGS. 13 and 18, atmospheric gas may be entrained into the venturi 290 through the inlet 291 and interrupt the stream of the control flow across the venturi 290. Interrupting the control flow in the venturi 290 may prevent the control flow from entering the fluid conduit 216 and, as a result, allow the medication in the reservoir 282 to be transported into the fluid conduit 216 and into the aerosol jet for nebulization. Except that the inlet 291 of the venturi 290 is inverted to face the bottom opening of the body 280, the operational characteristics of the venturi 290 associated with the control flow may be similar to the embodiments described above and, therefore, a detailed description of the venturi 290 is omitted herein.

According to another aspect of the invention, the nebulizer 200 may comprise a manual override mechanism (such as the mechanism 90 described above with reference to FIGS. 1 and 2) that may enable a user to override the breath actuation function of the nebulizer 200 to continuously generate aerosol. In various exemplary embodiments, the override mechanism may include a bypass conduit that connects the opening 372 of the gas line 371 to atmosphere. A suitable valve may be disposed in the bypass conduit to selectively open and close the bypass conduit. When the override mechanism is actuated, the valve may open the bypass conduit to vent the control flow drawn from the opening 372 to atmosphere. As a result, the control flow may no longer reach the fluid sleeve 213, regardless of whether the patient is inhaling or not. Thus, the breath actuation function of the nebulizer 200 may be disabled, and the nebulized medication may be continuously generated. When the override mechanism is not actuated, the valve may be biased in a closed position to enable the breath actuation function of the nebulizer 200. In some exemplary embodiments, the valve may also function as a control flow regulator for maintaining the control flow within a certain flow rate range. For example, the valve may be configured such that, when the flow rate of the control flow exceeds a predetermined threshold value, the valve may open the bypass conduit to vent excess flow out to atmosphere to maintain the control flow within the desired range. In addition or alternative to a valve, the through-hole 85 described above with reference to FIG. 3 may be used. As discussed above, maintaining the flow rate of the control flow within a certain range may be important to, for example, maintain actuation sensitivity and minimize fluid bubbling in the reservoir 282.

Figure 19:
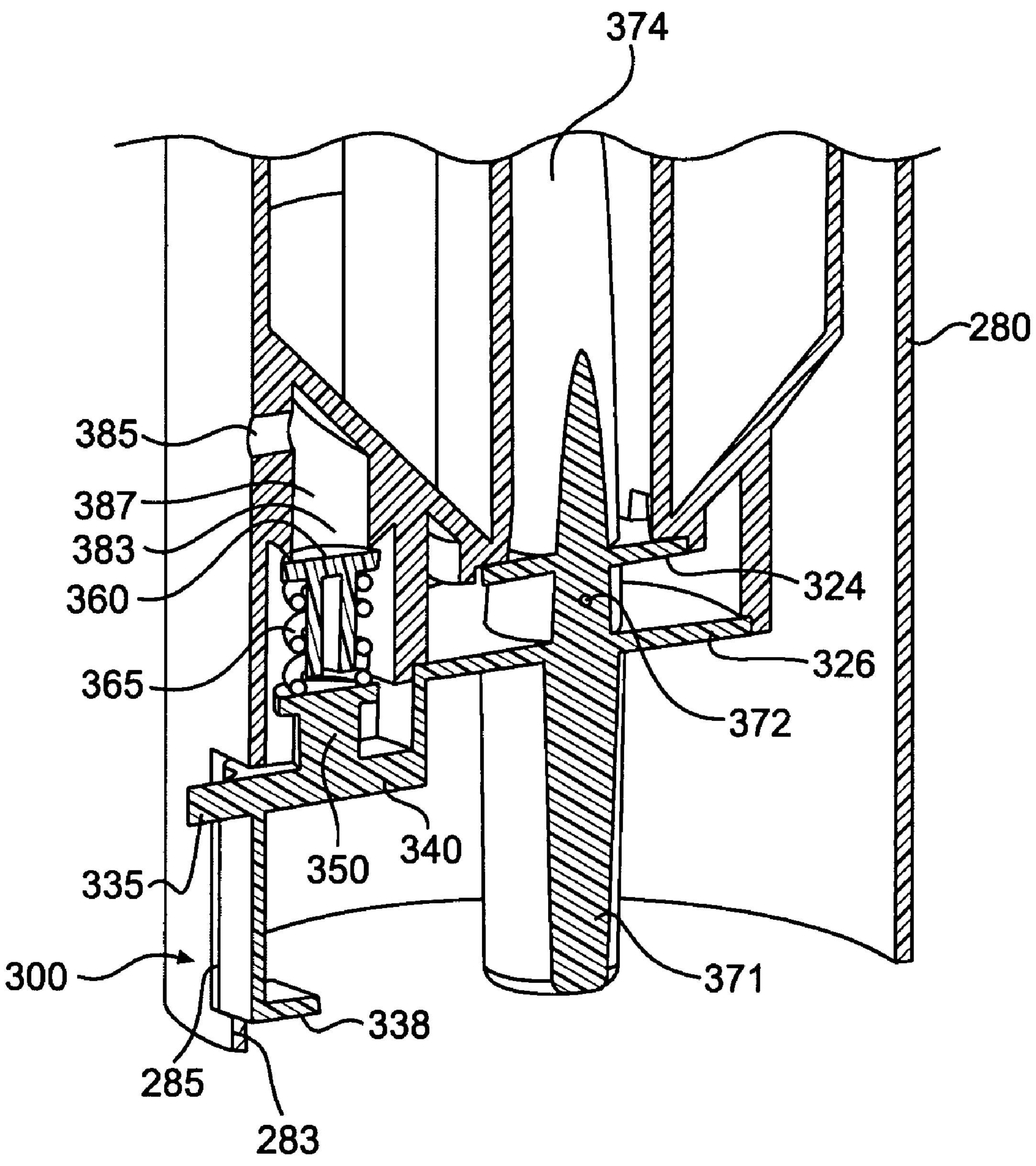
FIGS. 19 and 20 are partial cross-sectional, schematic views of the nebulizer of FIG. 11, illustrating a manual override mechanism in an unactivated state and an activated state, respectively, according to an exemplary embodiment of the invention.
Figure 20:
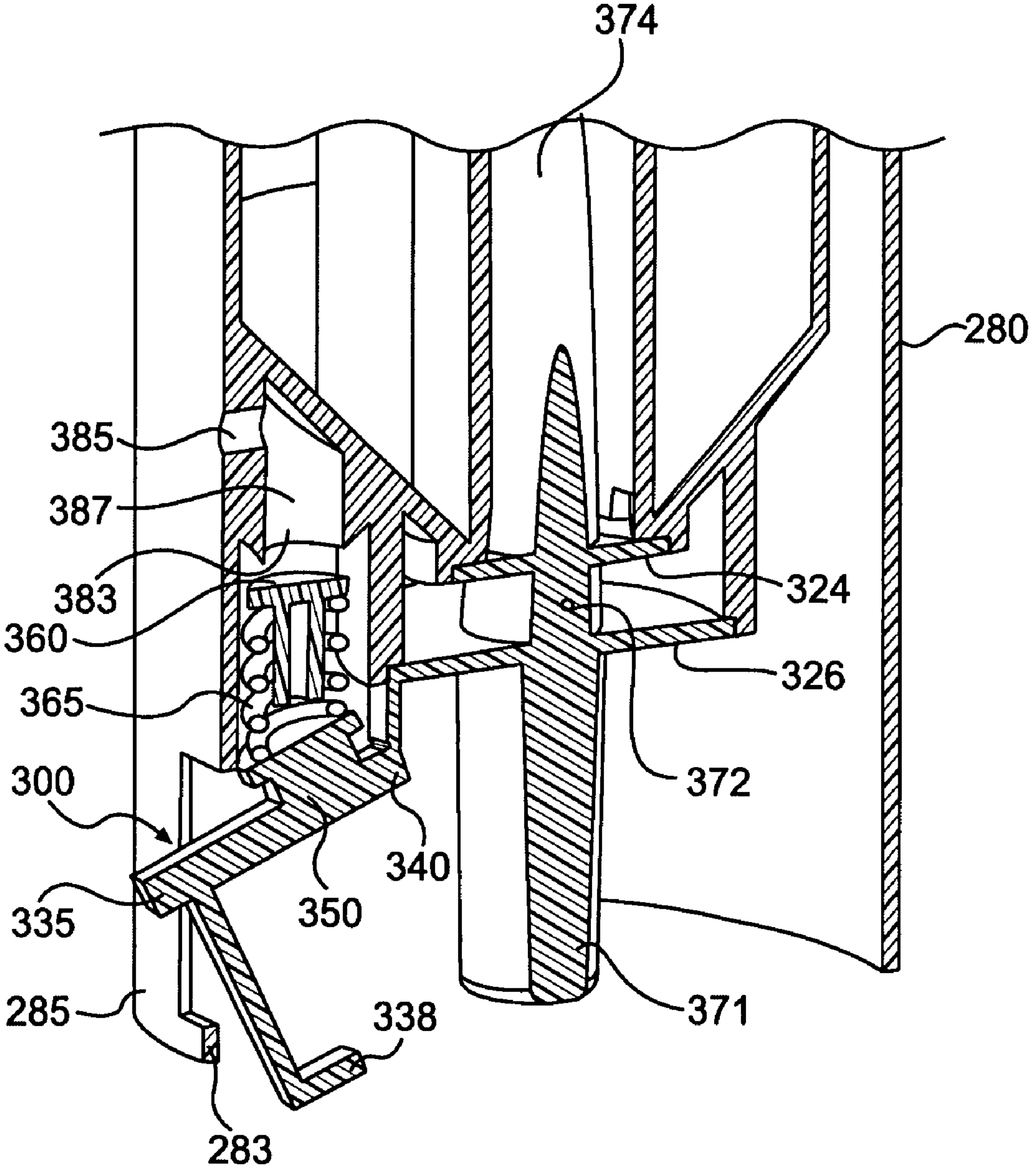

FIGS. 19 and 20 show an exemplary embodiment of the manual override mechanism 300. The override mechanism 300 may comprise a bypass conduit 387 having an inlet port 385 in fluid communication with a portion of the control flow channel (e.g., prior to entering the venturi 290) and an exit port 383 in fluid communication with atmosphere. The override mechanism 300 may comprise a valve assembly having a float 360 configured to open and close the exit port 383. The float 360 may be supported by a cylindrical member 350 extending from a lever 340 structurally associated with, yet movable relative to, a portion of the nozzle 374 or the gas line 371. In this embodiment shown in FIGS. 19 and 20, the lever 340 may be connected to the second annular flange 326 via a hinge (e.g., a live hinge). In an alternative embodiment, the lever 340 may be slidably coupled to the second annular flange 326. In another alternative embodiment, the lever 340 may be integrally or removably connected to any other structure of the nebulizer 200.

A spring member 365 may be disposed between the float 360 and the cylindrical member 350 to push the float 360 against the exit port 383. The spring 365 may function as an attachment member to attach the float 360 to the cylindrical member 350. For example, in one embodiment, one end of the spring 365 may be attached to the cylindrical member 350, while the other end is attached to the float 360.

The lever 340 may include a push tab 335 and an L-shaped extension configured to be seated into the opening 285 or slot of the body 280 with a bottom portion 338 abutting against two fingers 283 of the body 280. As shown in FIG. 19, when the L-shaped extension is seated in the opening 285, the exit port 383 of the bypass conduit 387 may be closed by the float 360, and the nebulizer 200 can be operated normally in the breath actuation mode. To override the breath actuation function, a user may push the push tab 335 inwardly to release the L-shaped extension out of the opening 285, as shown in FIG. 20. Pushing the push tab 335 may cause the lever 340 to be displaced downwardly. The displacement of the lever 340 may cause the float 360 to move down and open the exit port 383, venting the control flow to atmosphere.

The opening 285 of the body 280 may open at the bottom, through which the push tab 335 may pass, so that the valve assembly including the lever 340 and the float 360 may be completely removed from the nebulizer 200. In this overriding mode, the control flow may not reach the fluid sleeve 213, resulting in a continuous generation of aerosol, irrespective of the patient's breath. The override mechanism 300 discussed herein or the general concept thereof may be employed in the previous embodiments described above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nebulizer comprising:

a body comprising a reservoir for holding medication;

a nozzle for emitting a jet of pressurized gas;

a fluid conduit in communication with the reservoir for delivery of the medication proximate the jet to produce an aerosol of medication;

a nebulizer outlet in communication with the body for delivery of the aerosol to a patient;

an entrainment passage for providing entrainment flow from atmosphere during inhalation by the patient; and a control conduit in fluid communication with the fluid conduit for delivery of a control gas to the fluid conduit to prevent the delivery of the medication proximate the jet, the control conduit comprising a gas passage proximate the entrainment passage to allow the control gas to flow across the entrainment passage, wherein, during the inhalation by the patient, the entrainment flow through the entrainment passage substantially prevents the control gas from flowing across the entrainment passage so as to interrupt the delivery of the control gas to the fluid conduit.

2. The nebulizer of claim 1, wherein the entrainment passage comprises a venturi.

3. The nebulizer of claim 2, wherein the venturi comprises an inlet in fluid communication with atmosphere and an outlet in fluid communication with an interior of the body.

4. The nebulizer of claim 2, wherein the gas passage is disposed proximate a throat of the venturi.

5. The nebulizer of claim 4, wherein the venturi comprises a recessed portion adjacent the throat to facilitate the interruption of the control gas across the entrainment passage.

6. The nebulizer of claim 2, wherein the venturi is disposed inside the body.

7. The nebulizer of claim 1, further comprising a flow guide positioned adjacent the gas passage and configured to prevent the control gas from flowing across the entrainment passage during the inhalation by the patient.

8. The nebulizer of claim 1, wherein the gas passage comprises:

an inlet port in fluid communication with the entrainment passage; and an outlet port in fluid communication with the entrainment passage;

wherein the gas passage is configured to transport the control gas from the inlet port to the outlet port across the entrainment passage.

9. The nebulizer of claim 8, wherein the inlet port and the outlet port are aligned in a direction substantially perpendicular to a longitudinal axis of the entrainment passage.

10. The nebulizer of claim 1, wherein the pressurized gas and the control gas are delivered from a same source of gas, the control gas being drawn from a main gas line that supplies the pressurized gas to the nozzle.

11. The nebulizer of claim 10, further comprising a control flow manifold configured to direct the control gas drawn from the main gas line to the control conduit.

12. The nebulizer of claim 11, wherein the control flow manifold comprises an opening in the main gas line.

13. The nebulizer of claim 1, further comprising a flow regulator for controlling a flow of the control gas.

14. The nebulizer of claim 13, whether the flow regulator comprises a through-hole in a sleeve that at least partially defines the fluid conduit.

15. The nebulizer of claim 13, wherein the flow regulator comprises a valve disposed over an orifice in fluid communication with the control conduit, the valve being configured to open the orifice to vent excess control flow when the control gas flowing through the control conduit exceeds a threshold value.

16. The nebulizer of claim 1, wherein the gas passage comprises:

an inlet port; and an outlet port facing the inlet port;

wherein the gas passage is configured to transport the control gas from the inlet port to the outlet port across the entrainment passage, wherein the nebulizer further comprises a flow stopper movable between a first position, in which the stopper permits the flow of the control gas between the inlet and outlet ports, and a second position, in which the stopper substantially prevents the flow of the control gas across the entrainment passage, and wherein the inhalation by the patient causes the stopper to move from the first position to the second position.

17. The nebulizer of claim 16, wherein the movement of the flow stopper is controlled by a valve that moves in response to a patient's breath.

18. The nebulizer of claim 1, further comprising a stationary diverter to which the jet of pressurized gas is directed.

19. The nebulizer of claim 1, further comprising an override mechanism configured to override breath actuation of the nebulizer.

20. The nebulizer of claim 19, wherein the nebulizer is configured to continuously generate the aerosol when the override mechanism is actuated.

21. The nebulizer of claim 19, wherein the override mechanism comprises:
- a bypass conduit connecting between the control conduit and atmosphere; and
- a valve disposed in the bypass conduit to open and close the bypass conduit,
- wherein, upon actuation of the override mechanism, the valve opens the bypass conduit to vent the control gas from the control conduit to atmosphere, so as to prevent the delivery of the control gas to the fluid conduit.

22. A nebulizer comprising:
- a body comprising a reservoir for holding medication;
- a nozzle for emitting a jet of pressurized gas;
- a fluid conduit in communication with the reservoir for delivery of the medication proximate the jet to produce an aerosol of medication;
- a nebulizer outlet in communication with an interior of the body for delivery of the aerosol to a patient;
- a control conduit in fluid communication with the fluid conduit for delivery of a control gas to the fluid conduit to prevent the delivery of the medication proximate the jet, a portion of the control conduit permitting a flow of the control gas across a gap; and
- a flow stopper movable between a first position, in which the stopper is disposed out of the gap to permit the flow of the control gas across the gap, and a second position, in which the stopper is disposed in the gap to substantially prevent the flow of the control gas across the gap;
- wherein the inhalation by the patient causes the stopper to move from the first position to the second position.

23. The nebulizer of claim 22, wherein the movement of the flow stopper is controlled by a variable area orifice valve that actuates in response to the patient's inhalation.

24. The nebulizer of claim 22, wherein the flow stopper comprises a plate member movably disposed in and out of the gap.

25. The nebulizer of claim 22, wherein the portion of the control conduit is disposed in an entrainment passage that provides entrainment flow from atmosphere during the inhalation by the patient.

26. The nebulizer of claim 22, wherein the portion of the control conduit comprises an inlet port and an outlet port facing the inlet port, so as to transport the control gas from the inlet port to the outlet port, wherein a space between the inlet and outlet ports defines the gap.

27. The nebulizer of claim 22, wherein the pressurized gas and the control gas are delivered from a same source of gas, the control gas being drawn from a main gas line that supplies the pressurized gas to the nozzle.

28. The nebulizer of claim 27, further comprising a control flow manifold configured to direct the control gas drawn from the main gas line to the control conduit.

29. The nebulizer of claim 22, further comprising a flow regulator for controlling a flow of the control gas.

30. The nebulizer of claim 29, whether the flow regulator comprises a through-hole in a sleeve that at least partially defines the fluid conduit.

31. The nebulizer of claim 22, further comprising a stationary diverter to which the jet of pressurized gas is directed.

32. The nebulizer of claim 22, further comprising an override mechanism configured to override breath actuation of the nebulizer.

33. The nebulizer of claim 32, wherein the override mechanism comprises:
- a bypass conduit connecting between the control conduit and atmosphere; and
- a valve disposed in the bypass conduit to open and close the bypass conduit,
- wherein, upon actuation of the override mechanism, the valve opens the bypass conduit to vent the control gas from the control conduit to atmosphere, so as to prevent the delivery of the control gas to the fluid conduit.

34. A method of controlling a nebulization process, comprising:
- providing medication in a reservoir within a body, the body comprising an outlet for delivery of medication to a patient and an entrainment passage for providing entrainment flow from atmosphere during inhalation by the patient;
- emitting a jet of pressurized gas into the body;
- providing a fluid conduit in communication with the reservoir for delivery of the medication proximate the jet;
- preventing delivery of the medication proximate the jet by delivering a control gas to the fluid conduit via a control conduit, the control conduit comprising a gas passage proximate the entrainment passage to allow the control gas to flow across the entrainment passage; and
- interrupting the flow of the control gas across the entrainment passage to prevent the delivery of the control gas to the control conduit, the interruption permitting delivery of the medication proximate the jet to produce an aerosol of medication.

35. The method of claim 34, wherein, during the inhalation by the patient, the entrainment flow through the entrainment passage substantially interrupts the flow of the control gas across the entrainment passage.

36. The method of claim 34, wherein the entrainment passage comprises a venturi.

37. The method of claim 36, wherein the gas passage is disposed proximate a throat of the venturi.

38. The nebulizer of claim 34, further comprising providing a flow guide adjacent the gas passage proximate the entrainment passage to prevent the control gas from flowing across the entrainment passage during the inhalation by the patient.

39. The method of claim 34, wherein the gas passage comprises:
- an inlet port in fluid communication with the entrainment passage; and
- an outlet port in fluid communication with the entrainment passage;
- wherein the gas passage is configured to transport the control gas from the inlet port to the outlet port across the entrainment passage.

40. The method of claim 39, further comprising providing a flow stopper movable between a first position, in which the stopper permits the flow of the control gas between the inlet and outlet ports, and a second position, in which the stopper substantially prevents the flow of the control gas across the entrainment passage, wherein the inhalation by the patient causes the stopper to move from the first position to the second position.

41. The method of claim 34, wherein the pressurized gas and the control gas are delivered from a same source of gas, the control gas being drawn from a main gas line that supplies the pressurized gas.

42. The method of claim 34, further comprising regulating a flow of the control gas to the control conduit via a flow regulator.

43. The method of claim 42, wherein the flow regulator comprises a valve disposed over an orifice in fluid communication with the control conduit, the valve being configured to open the orifice to vent excess control flow when the control gas flowing through the control conduit exceeds a threshold value.

44. The method of claim 34, further comprising regulating a flow of the control gas via a through-hole in a sleeve that at least partially defines the fluid conduit.

45. The method of claim 34, further comprising directing the jet of pressurized gas towards a stationary diverter.

46. The method of claim 34, further comprising overriding the control of the nebulization process to continuously generate the aerosol of medication.

47. The method of claim 46, wherein the overriding comprises:

providing a bypass conduit connecting between the control conduit and atmosphere;

disposing a valve in the bypass conduit; and opening the valve to open the bypass conduit so as to vent the control gas from the control conduit to atmosphere.

48. A method of controlling a nebulization process, comprising:

providing medication in a reservoir within a body, the body comprising an outlet for delivering medication to a patient;

emitting a jet of pressurized gas into the body;

providing a fluid conduit in communication with the reservoir for delivery of the medication proximate the jet;

preventing delivery of the medication proximate the jet by delivering a control gas to the fluid conduit via a control conduit, a portion of the control conduit permitting a flow of the control gas across a gap;

providing a flow stopper movable between a first position, in which the stopper is disposed out of the gap to permit the flow of the control gas across the gap, and a second position, in which the stopper is disposed in the gap to substantially prevent the flow of the control gas across the gap; and interrupting the flow of the control gas across the gap by the flow stopper to prevent the delivery of the control gas to the control conduit, the interruption permitting delivery of the medication proximate the jet to produce an aerosol of medication.

49. The method of claim 48, wherein the flow stopper is movable from the first position to the second position in response to inhalation by the patient.

50. The method of claim 49, wherein the movement of the flow stopper is controlled by a valve that actuates in response to the patient's inhalation.

51. The method of claim 49, wherein the portion of the control conduit is disposed in an entrainment passage that provides entrainment flow from atmosphere during the inhalation by the patient.

52. The method of claim 48, wherein the flow stopper comprises a plate member movably disposed in and out of the gap.

53. The method of claim 48, wherein the portion of the control conduit comprises an inlet port and an outlet port facing the inlet port, so as to transport the control gas from the inlet port to the outlet port, wherein a space between the inlet and outlet ports defines the gap.

54. The method of claim 48, wherein the pressurized gas and the control gas are delivered from a same source of gas, the control gas being drawn from a main gas line that supplies the pressurized gas.

55. The method of claim 48, further comprising regulating a flow of the control gas to the control conduit via a flow regulator.

56. The method of claim 55, wherein the flow regulator comprises a valve disposed over an orifice in fluid communication with the control conduit, the valve being configured to open the orifice to vent excess control flow when the control gas flowing through the control conduit exceeds a threshold value.

57. The method of claim 48, further comprising regulating a flow of the control gas via a through-hole in a sleeve that at least partially defines the fluid conduit.

58. The method of claim 48, further comprising directing the jet of pressurized gas towards a stationary diverter.

59. The method of claim 48, further comprising overriding the control of the nebulization process to continuously generate the aerosol of medication.

60. The method of claim 59, wherein the overriding comprises:

providing a bypass conduit connecting between the control conduit and atmosphere;

disposing a valve in the bypass conduit; and opening the valve to open the bypass conduit so as to vent the control gas from the control conduit to atmosphere.

* * * * *